(12) United States Patent
Katsuhara

(10) Patent No.: US 12,619,670 B2
(45) Date of Patent: May 5, 2026

(54) CONTENT RECOMMENDATION SYSTEM, CONTENT RECOMMENDATION METHOD, CONTENT LIBRARY, METHOD FOR GENERATING CONTENT LIBRARY, AND TARGET-INPUT USER INTERFACE

(71) Applicant: SONY GROUP CORPORATION, Tokyo (JP)

(72) Inventor: Mao Katsuhara, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 178 days.

(21) Appl. No.: 18/548,930

(22) PCT Filed: Jan. 26, 2022

(86) PCT No.: PCT/JP2022/002893
§ 371 (c)(1),
(2) Date: Sep. 5, 2023

(87) PCT Pub. No.: WO2022/190686
PCT Pub. Date: Sep. 15, 2022

(65) Prior Publication Data
US 2025/0307324 A1 Oct. 2, 2025

(30) Foreign Application Priority Data
Mar. 10, 2021 (JP) ................................. 2021-038000

(51) Int. Cl.
*G06F 16/9535* (2019.01)
*A61B 5/16* (2006.01)

(52) U.S. Cl.
CPC .......... *G06F 16/9535* (2019.01); *A61B 5/165* (2013.01)

(58) Field of Classification Search
CPC ............................. G06F 16/9535; A61B 5/165
See application file for complete search history.

(56) References Cited

U.S. PATENT DOCUMENTS

| | | | | |
|---|---|---|---|---|
| 12,029,573 B2 * | 7/2024 | Garten | ................... | G16H 50/20 |
| 2016/0034663 A1 * | 2/2016 | Nino | ...................... | G16H 10/60 |
| | | | | 705/2 |

(Continued)

FOREIGN PATENT DOCUMENTS

| | | |
|---|---|---|
| JP | 2007-323171 A | 12/2007 |
| JP | 2013-054447 A | 3/2013 |

(Continued)

OTHER PUBLICATIONS

International Search Report and Written Opinion of PCT Application No. PCT/JP2022/002893, issued on Apr. 12, 2022, 09 pages of ISRWO.

*Primary Examiner* — Debbie M Le
(74) *Attorney, Agent, or Firm* — CHIP LAW GROUP

(57) ABSTRACT

Provided is A content recommendation system that includes a vital-feature-amount generator that acquires chronological vital data that is vital data of a user that is continuously and chronologically sensed by a vital sensor, and generates chronological vital-feature-amount data from the chronological vital data. The content recommendation system further includes an emotion estimation calculator that generates, from the chronological vital-feature-amount data, an estimated emotion value that is an estimated value of an emotion of the user, a recommendation engine that acquires a target emotion value that is input through a user interface terminal apparatus and indicates an emotion that is a target of the user, and selects, from a content library, content used to reach the target emotion value from the estimated emotion value, and a content recommendation section that recommends the selected content to the user interface terminal apparatus.

29 Claims, 8 Drawing Sheets

(56)        References Cited

U.S. PATENT DOCUMENTS

2017/0351768 A1   12/2017   Nagao
2018/0113987 A1*   4/2018   Zhu ........................ G16H 40/63
2018/0336276 A1   11/2018   Fukino

FOREIGN PATENT DOCUMENTS

JP       2016-146173 A     8/2016
JP       2016-532360 A    10/2016
JP       2018-159908 A    10/2018
JP       2018-195043 A    12/2018

* cited by examiner

Base screen                    Current display                    Swipe
                                                                (User input)

|   | ①' | ②' | ③' | ④' |
|---|---|---|---|---|
| ① |   |   |   |   |
| ② |   |   |   |   |
| ③ |   |   |   |   |
| ④ |   |   |   |   |

CONTENT RECOMMENDATION SYSTEM, CONTENT RECOMMENDATION METHOD, CONTENT LIBRARY, METHOD FOR GENERATING CONTENT LIBRARY, AND TARGET-INPUT USER INTERFACE

CROSS REFERENCE TO RELATED APPLICATIONS

This application is a U.S. National Phase of International Patent Application No. PCT/JP2022/002893 filed on Jan. 26, 2022, which claims priority benefit of Japanese Patent Application No. JP 2021-038000 filed in the Japan Patent Office on Mar. 10, 2021. Each of the above-referenced applications is hereby incorporated herein by reference in its entirety.

TECHNICAL FIELD

The present disclosure relates to a content recommendation system that recommends content such as a piece of music to a user interface terminal apparatus, and a content recommendation method. The present disclosure relates to a content library used to select content to be recommended, and a method for generating the content library. The present disclosure relates to a target-input user interface that is a graphical user interface displayed on the user interface terminal apparatus.

BACKGROUND ART

Typically, when content such as a piece of music and a video is recommended, meta-information including the behavior of a user such as a shopping history or a viewing history of the user; as well as a genre, a rhythm, and a tempo of a piece of music is used to generate a recommendation list for each scene according to a general interpretation, and the generated recommendation list is presented.

CITATION LIST

Patent Literature

Patent Literature 1: Japanese Patent Application Laid-open No. 2018-195043
Patent Literature 2: Japanese Unexamined Patent Application Publication No. 2016-532360
Patent Literature 3: Japanese Patent Application Laid-open No. 2018-159908

DISCLOSURE OF INVENTION

Technical Problem

However, the use of the above-described recommendation method based on generalities results in difficulty in knowing a true intention of a user. A recommendation against an intention of a user may result in a reduction in the level of user's confidence in a recommendation system. Consequently, there is a possibility that the service will not be used by the user.

For this reason, recommendations of content depending on a psychological state of each user have been proposed (Patent Literature 1 and Patent Literature 2). However, those methods are methods for actually making a recommendation using estimation, and thus have little scientific basis. Further, content to be recommended is selected on the basis of conventional meta-information. This results in difficulty in recommending content fit for each user.

In view of the circumstances described above, it is an object of the present disclosure to recommend content fit for each user.

Solution to Problem

A content recommendation system according to an embodiment of the present disclosure includes:
a vital-feature-amount generator that
acquires chronological vital data that is vital data of a user that is continuously and chronologically sensed by a vital sensor, and
generates chronological vital-feature-amount data from the chronological vital data;
an emotion estimation calculator that generates, from the chronological vital-feature-amount data, an estimated emotion value that is an estimated value of an emotion of the user;
a recommendation engine that
acquires a target emotion value that is input through a user interface terminal apparatus and indicates an emotion that is a target of the user, and
selects, from a content library, content used to reach the target emotion value from the estimated emotion value; and
a content recommendation section that recommends the selected content to the user interface terminal apparatus.

The present embodiment makes it possible to reflect continuous and chronological vital data for a longer period of time. This results in being able to generate an estimated emotion value more precisely. Since the estimated emotion value is more precise, content more suitable for reaching a target emotion value from the estimated emotion value can be selected.

Before the recommendation engine acquires the target emotion value,
the vital-feature-amount generator may acquire the chronological vital data to generate the chronological vital-feature-amount data, and
the emotion estimation calculator may generate the estimated emotion value on the basis of the chronological vital-feature-amount data.

Before the recommendation engine acquires a target emotion value, the vital-feature-amount generator acquires chronological vital data to generate chronological vital-feature-amount data, and the emotion estimation calculator generates an estimated emotion value on the basis of the chronological vital-feature-amount data. This makes it possible to reflect continuous and chronological vital data for a longer period of time, compared to when the recommendation engine acquires a target emotion value, and then, chronological vital data is acquired to generate chronological vital-feature-amount data and an estimated emotion value is generated. This results in being able to generate an estimated emotion value more precisely. Since the estimated emotion value is more precise, content more suitable for reaching a target emotion value from the estimated emotion value can be selected.

The emotion estimation calculator may generate the estimated emotion value on the basis of newest vital-feature-amount data included in the chronological vital-feature-amount data, the newest vital-feature-amount data being obtained by previous vital-feature-amount data included in the chronological vital-feature-amount data being changed.

Not only newest vital-feature-amount data but also chronological vital-feature-amount data (that is, including previous vital-feature-amount data) is input to the emotion estimation calculator. The emotion estimation calculator generates an estimated emotion value on the basis of newest vital-feature-amount data included in chronological vital-feature-amount data, the newest vital-feature-amount data being obtained by previous vital-feature-amount data included in the chronological vital-feature-amount data being changed. In other words, the emotion estimation calculator generates a current estimated value of an emotion of a user, the value including information indicating how the previous vital-feature-amount data has been changed to the newest vital-feature-amount data. In other words, the emotion estimation calculator generates a current estimated value of an emotion of a user, the value including information indicating how previous vital-feature-amount data has been changed in a plurality of phases. This makes it possible to reflect continuous and chronological vital data for a longer period of time. This results in being able to generate an estimated emotion value more precisely.

The content library may store therein at least one piece of content used to reach each one of a plurality of the different target emotion values from a corresponding one of a plurality of the different estimated emotion values.

The recommendation engine can select all of a plurality of pieces of content used to reach a target emotion value from an estimated emotion value.

The content library may be in the form of a two-dimensional matrix that includes the plurality of the different estimated emotion values and the plurality of the different target emotion values, and at least one piece of content used to reach each one of the plurality of the different target emotion values from a corresponding one of the plurality of the different estimated emotion values, may be registered in a portion corresponding to a point of intersection of lines corresponding to the one of the plurality of the different target emotion values and the corresponding one of the plurality of the different estimated emotion values.

The recommendation engine can select all of a plurality of pieces of content registered in a portion corresponding to a point of intersection of lines corresponding to an estimated emotion value and a target emotion value.

The recommendation engine may select a plurality of pieces of content from the content library, the content recommendation system may further include:

a context information generator that generates context information regarding the user; and a context processor that narrows down the plurality of selected pieces of content to at least one piece of content on the basis of the context information, and the content recommendation section may recommend the at least one piece of content obtained by the narrowing down.

On the basis of piece of context information generated by the context information generator, the context processor of the cloud server narrows down plurality of pieces of content selected by the recommendation engine to at least one piece of content. Typically, the context processor narrows down pieces of content to one piece of content. However, the context processor may narrow down pieces of content to a plurality of pieces of content.

The content library may store therein a plurality of pieces of content used to reach each one of a plurality of the different target emotion values from a corresponding one of a plurality of the different estimated emotion values, the different pieces of context information of a plurality of the different pieces of context information may be respectively associated with pieces of content of the plurality of pieces of content, and the context processor may narrow down the plurality of selected pieces of content to at least one piece of content with which the piece of generated context information is associated.

Different pieces of context information of a plurality of different pieces of context information are respectively associated with pieces of content of a plurality of pieces of content registered in the content library. The context processor narrows down a plurality of selected pieces of content to at least one piece of content with which a piece of context information generated by the context information generator is associated. For example, the recommendation engine selects a piece of content with which "during taking exercise" is associated as a piece of context information, and selects a piece of content with which "at the time of going to bed" is associated as a piece of context information. When the piece of context information generated by the context information generator is "during taking exercise", the context processor narrows down pieces of content to the piece of content with which "during taking exercise" is associated as a piece of context information. The context processor may narrow down pieces of content not only on the basis of context information, but also on the basis of chronological vital data and metadata of content. For example, the context processor may narrow down pieces of content to a piece of content (a piece of music) to which heartbeat of a user and its tempo that are included in chronological vital data synchronize.

From the chronological vital-feature-amount data obtained after the content is recommended, the emotion estimation calculator may generate an estimated emotion value after recommendation that is the estimated value of an emotion of the user, and the content recommendation system may further include a library update section that updates the content library for each user by registering the recommended content in the content library for each user as content used to reach, from the estimated emotion value, the estimated emotion value after recommendation.

As described above, the library update section gives feedback on the content library every time a piece of content is recommended. This makes it possible to change an initial content library to a tailored content library customized for each user.

From the chronological vital-feature-amount data obtained after the content is recommended, the emotion estimation calculator may generate an estimated emotion value after recommendation that is the estimated value of an emotion of the user, the recommendation engine may further select, from the content library, content used to reach the target emotion value from the estimated emotion value after recommendation, and the content recommendation section may recommend the further selected content to the user interface terminal apparatus.

An emotion of a user is desired to reach a target emotion value after the user experiences (for example, viewing of) content. In other words, an estimated emotion value after recommendation is desired to reach a target emotion value. On the other hand, there is a possibility that the experience in recommended content will not effectively act on a change in the emotion of the user and the estimated emotion value after recommendation will not reach the target emotion value. For example, there is a possibility that the estimated emotion value after recommendation will remain unchanged or reach an unexpected emotion value. The calculation of an estimated emotion value after recommendation makes it possible to give feedback on whether recommended content has effectively acted on a change in an emotion of a user (that is, whether a target emotion value has been reached).

The emotion estimation calculator may generate the estimated emotion values obtained in chronological order, and the recommendation engine may select, from the content library, content used to reach the target emotion value from a newest estimated emotion value that is included in the estimated emotion values obtained in chronological order, the newest estimated emotion value being reached from a previous estimated emotion value that is included in the estimated emotion values obtained in chronological order.

The recommendation engine can select content that is used to reach a target emotion value that includes information indicating how a previous estimated emotion value has been changed to a newest estimated emotion value.

The content library may store therein at least one piece of content used to reach the target emotion value from the newest estimated emotion value included in the estimated emotion values obtained in chronological order, the newest estimated emotion value being reached from the previous estimated emotion value included in the estimated emotion values obtained in chronological order.

Such a configuration of the content library enables the recommendation engine to select, from the content library, content used to reach a target emotion value from a newest estimated emotion value that is included in estimated emotion values obtained in chronological order, the newest estimated emotion value being reached from a previous estimated emotion value (for example, ten minutes ago) that is included in the estimated emotion values obtained in chronological order.

The content library may store therein at least one piece of content used to reach, from each one of a plurality of the different previous estimated emotion values, a corresponding one of a plurality of the different newest estimated emotion values and to reach, from the corresponding one of the plurality of the different newest estimated emotion values, a corresponding one of a plurality of the different target emotion values.

Such a configuration of the content library enables the recommendation engine to select content used to reach a target emotion value in a plurality of phases, where the target emotion value is reached from a newest estimated emotion value that is reached from a previous estimated emotion value.

The content library may be in the form of a three-dimensional matrix that includes the plurality of the different previous estimated emotion values, the plurality of the different newest estimated emotion values, and the plurality of the different target emotion values, and at least one piece of content used to reach, from each one of the plurality of the previous estimated emotion values, a corresponding one of the plurality of the newest estimated emotion values and to reach, from the corresponding one of the plurality of the newest estimated emotion values, a corresponding one of the plurality of the target emotion values, may be registered in a portion corresponding to a point of intersection of lines corresponding to the one of the plurality of the previous estimated emotion values, the corresponding one of the plurality of the newest estimated emotion values, and the corresponding one of the plurality of the target emotion values.

Such a configuration of the content library enables the recommendation engine to select content used to reach a target emotion value in a plurality of phases, where the target emotion value is reached from a newest estimated emotion value that is reached from a previous estimated emotion value.

The emotion estimation calculator may calculate a probability of the user having an emotion in a specific emotional state, and sets the probability to be the estimated emotion value.

The use of the probability, which is different from the degree and is represented by a statistical and probabilistic value makes it possible to calculate an appropriate estimated emotion value.

The probability may correspond to a value obtained by quantifying a state of the user having an emotion in the specific emotional state.

The use of a value obtained by quantification makes it possible to estimate an emotion of a user more scientifically.

The emotion estimation calculator
may calculate a first probability that is a probability of the user having an emotion in a first specific emotional state, and a second probability that is a probability of the user having an emotion in a second specific emotional state, and
may generate the estimated emotion value on the basis of the first probability and the second probability.

The calculation of probabilities in a plurality of types of emotional states results in increasing the possibility of being able to estimate an emotion of a user more precisely.

The first specific emotional state may be an arousal state, the first probability may be a probability of the user having an emotion in the arousal state, the second specific emotional state may be a pleasure state of valance, and the second probability may be a probability of the user having an emotion in the pleasure state.

The emotion estimation calculator uses a model that uses the Russell's circumplex model. However, the model of the emotion estimation calculator is not exactly the Russell's circumplex model. The use of the "probability", which is different from the "degree" adopted in the Russell's circumplex model makes it possible to estimate an emotion of a user more scientifically.

The user interface terminal apparatus may display a target-input user interface that is a GUI displayed for the user to input the target emotion value,
the target-input user interface may display thereon, in a single-axis direction, a plurality of different areas respectively corresponding to high and low probabilities in the specific emotional state, and
the user may select one of the plurality of different areas to input the probability situated in the selected one of the plurality of different areas to the user interface terminal apparatus as the target emotion value.

A user can visually select a target area easily by viewing a coordinate system of the target-input user interface.

The target-input user interface may display thereon a plurality of different areas in a matrix in a biaxial direction, the plurality of different areas being a plurality of different areas respectively corresponding to a combination of a high first probability and a high second probability, a combination of the high first probability and a low second probability, a combination of a low first probability and the low second probability, and a combination of the low first probability and the high second probability, the first probability being a probability of the user having an emotion in a first specific emotional state, the second probability being a probability of the user having an emotion in a second specific emotional state, and the user may select one of the plurality of different areas to input, to the user interface terminal apparatus and as the target emotion value, a combination of the first and second probabilities situated in the selected one of the plurality of different areas.

A user can visually select a target area easily by viewing a coordinate system in a matrix in a biaxial direction.

The user interface terminal apparatus may acquire the generated estimated emotion value, and the target-input user interface may display an object representing the estimated emotion value on an area that is included in the plurality of different areas and in which the estimated emotion value is situated.

When a user views an object displayed on an area, the user understands a relative location of the area in the entirety of a coordinate system, where the object representing an estimated emotion value is displayed on the area. A user who is used to viewing the target-input user interface visually understands a current emotion of the user. Further, the user understands a relative evaluation of his/her current emotion. This enables the user to easily determine his/her target emotion. For example, when the user views a coordinate system of the target-input user interface, the user easily thinks of causing his/her emotion to reach another area of a target from a current area.

The user may input the target emotion value to the user interface terminal apparatus by swiping from the area displaying thereon the object representing the estimated emotion value to an area that is included in the plurality of different areas and in which the target emotion value is situated.

The swiping enables a user to intuitively input reaching of a current emotion to a feeling that the user wants to have.

On respective areas of the plurality of different areas respectively corresponding to high and low probabilities in the specific emotional state, the target-input user interface may display pictograms that represent respective emotional states respectively representing the high and low probabilities.

The user can easily determine his/her target emotion by viewing a pictogram. Further, the user visually understands his/her current emotion easily when an object (a star-shaped mark in this example) representing an estimated value of an emotion of the user is displayed on a coordinate system on which a pictogram is displayed.

The content library may be generated by a process including acquiring pieces of chronological vital data of a plurality of subjects in a controlled environment, the pieces of chronological vital data being continuously and chronologically sensed by the respective vital sensors, generating pieces of chronological vital-feature-amount data of the plurality of subjects from the pieces of chronological vital data of the plurality of subjects, generating estimated emotion values of the plurality of subjects from the pieces of chronological vital-feature-amount data of the plurality of subjects, causing each of the plurality of subjects to experience a piece of content in the controlled environment, generating the pieces of chronological vital-feature-amount data of the plurality of subjects from the pieces of chronological vital data of the plurality of subjects after experiencing the respective pieces of content, from the pieces of chronological vital-feature-amount data of the plurality of subjects after experiencing the respective pieces of content, generating the estimated emotion values obtained after subjects of the plurality of subjects experience the respective pieces of content, and registering the piece of experienced content in the content library as a piece of content used to reach, from the estimated emotion value, the estimated emotion value obtained after the subject experiences the piece of content.

This makes it possible to scientifically generate an appropriate initial content library without only depending on, for example, metadata or tempo of content.

The vital sensor may be included in a wearable device, and the vital sensor may acquire, as the vital data, data of brain waves, pulse waves, a pulse, a blood pressure, a blood flow, sweating, breathing, and/or a temperature by brain wave measurement, plethysmography, skin conductance measurement, laser Doppler, image-capturing performed using an RGB camera, and/or image-capturing performed using a thermographic camera.

The inclusion of the vital sensor in a wearable device enables the vital sensor to easily sense vital data of a user more continuously and chronologically.

The context information generator may generate the context information on the basis of the chronological vital-feature-amount data generated from the chronological vital data acquired by the vital sensor, environment data of an environment of the user, and/or an activity state of the user.

The context information generator of the cloud server can generate context information regarding a user on the basis of chronological vital data (such as brain waves, pulse waves, a pulse, a blood pressure, a blood flow, sweating, breathing, and/or a temperature), environment data (such as a temperature, humidity, and illumination intensity), and/or an activity state of the user (such as whether the user is taking exercise). The context information may include any kinds of context such as a time, a location, and details of activities (for example, during taking exercise, during going to work, being at work, during driving, at the time of getting out of bed, and at the time of going to bed).

From the chronological vital-feature-amount data and the context information, the emotion estimation calculator may generate the estimated emotion value that is the estimated value of an emotion of the user.

A more precise estimated emotion value can be generated, compared to when the emotion estimation calculator generates an estimated emotion value on the basis of only vital-feature-amount data (that is, without using context information).

A content recommendation method according to an embodiment of the present disclosure includes:

acquiring chronological vital data that is vital data of a user that is continuously and chronologically sensed by a vital sensor;

generating chronological vital-feature-amount data from the chronological vital data;

generating, from the chronological vital-feature-amount data, an estimated emotion value that is an estimated value of an emotion of the user;

acquiring a target emotion value that is input through a user interface terminal apparatus and indicates an emotion that is a target of the user;

selecting, from a content library, content used to reach the target emotion value from the estimated emotion value; and recommending the selected content to the user interface terminal apparatus.

A content library according to an embodiment of the present disclosure is generated by a process including:

acquiring pieces of chronological vital data of a plurality of subjects in a controlled environment, the pieces of chronological vital data being continuously and chronologically sensed by respective vital sensors;

generating pieces of chronological vital-feature-amount data of the plurality of subjects from the pieces of chronological vital data of the plurality of subjects;

generating estimated emotion values of the plurality of subjects from the pieces of chronological vital-feature-amount data of the plurality of subjects;

causing each of the plurality of subjects to experience a piece of content in the controlled environment;

generating the pieces of chronological vital-feature-amount data of the plurality of subjects from the pieces of chronological vital data of the plurality of subjects after experiencing the respective pieces of content;

from the pieces of chronological vital-feature-amount data of the plurality of subjects after experiencing the respective pieces of content, generating the estimated emotion values obtained after subjects of the plurality of subjects experience the respective pieces of content; and registering the piece of experienced content in the content library as a piece of content used to reach, from the estimated emotion value, the estimated emotion value obtained after the subject experiences the piece of content.

A method for generating a content library is a method according to an embodiment of the present disclosure and includes:

acquiring pieces of chronological vital data of a plurality of subjects in a controlled environment, the pieces of chronological vital data being continuously and chronologically sensed by respective vital sensors;

generating pieces of chronological vital-feature-amount data of the plurality of subjects from the pieces of chronological vital data of the plurality of subjects;

generating estimated emotion values of the plurality of subjects from the pieces of chronological vital-feature-amount data of the plurality of subjects;

causing each of the plurality of subjects to experience a piece of content in the controlled environment;

generating the pieces of chronological vital-feature-amount data of the plurality of subjects from the pieces of chronological vital data of the plurality of subjects after experiencing the respective pieces of content;

from the pieces of chronological vital-feature-amount data of the plurality of subjects after experiencing the respective pieces of content, generating the estimated emotion values obtained after subjects of the plurality of subjects experience the respective pieces of content; and registering the piece of experienced content in the content library as a piece of content used to reach, from the estimated emotion value, the estimated emotion value obtained after the subject experiences the piece of content.

A target-input user interface according to an embodiment of the present disclosure is a GUI displayed by a user interface terminal apparatus for a user to input a target emotion value, the user interface terminal apparatus being included in a content recommendation system that includes a vital-feature-amount generator that acquires chronological vital data that is vital data of a user that is continuously and chronologically sensed by a vital sensor, and generates chronological vital-feature-amount data from the chronological vital data, an emotion estimation calculator that generates, from the chronological vital-feature-amount data, an estimated emotion value that is an estimated value of an emotion of the user, a recommendation engine that acquires the target emotion value being input through the user interface terminal apparatus and indicating an emotion that is a target of the user, and selects, from a content library, content used to reach the target emotion value from the estimated emotion value, and a content recommendation section that recommends the selected content to the user interface terminal apparatus, the target-input user interface displaying thereon, in a single-axis direction, a plurality of different areas respectively corresponding to high and low probabilities in a specific emotional state, the user selecting one of the plurality of different areas, the probability situated in the selected one of the plurality of different areas being input to the user interface terminal apparatus as the target emotion value.

MODE(S) FOR CARRYING OUT THE INVENTION

Embodiments according to the present disclosure will now be described below with reference to the drawings.

I. FIRST EMBODIMENT

1. Overview of Content Recommendation System

Figure 1:
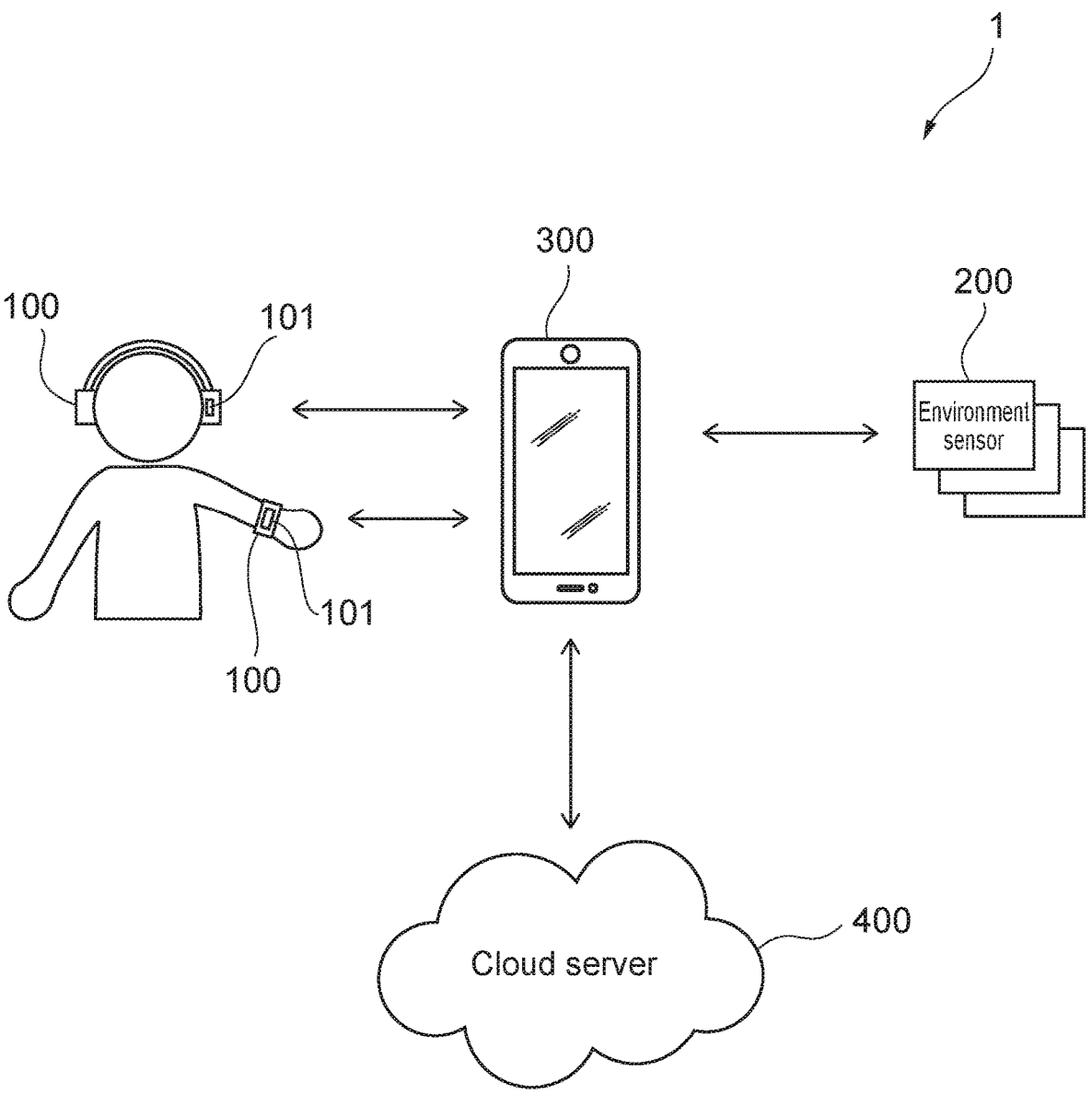
FIG. 1 illustrates an overview of a content recommendation system according to an embodiment of the present disclosure.

FIG. 1 illustrates an overview of a content recommendation system according to an embodiment of the present disclosure.

A content recommendation system 1 includes at least one wearable device 100, at least one environment sensor 200, a user interface terminal apparatus 300, and a cloud server 400.

Examples of the at least one wearable device 100 include ear pads, headphones, a smartwatch, a wristband fitness tracker, and a clothing wearable device. The at least one wearable device 100 is worn by one user. The at least one wearable device 100 is hereinafter collectively simply referred to as a wearable device 100. The wearable device 100 includes at least one vital sensor 101. The at least one vital sensor 101 is hereinafter collectively simply referred to as a vital sensor 101.

The vital sensor 101 continuously and chronologically senses vital data of a user who is wearing the wearable device 100. The vital sensor 101 acquires, as vital data, data of, for example, brain waves, pulse waves, a pulse, a blood pressure, a blood flow, sweating, breathing, and/or a temperature using an approach of, for example, brain wave measurement, plethysmography, skin conductance measurement, laser Doppler, image-capturing performed using an RGB camera, and/or image-capturing performed using a thermographic camera.

Examples of the at least one environment sensor 200 include a temperature sensor, a humidity sensor, and an illumination intensity sensor. The at least one environment sensor 200 is hereinafter collectively simply referred to as an environment sensor 200. The environment sensor 200 senses, for example, a temperature, humidity, and illumination intensity (environment data). The environment sensor 200 may be included in the user interface terminal apparatus 300, may be included in the wearable device 100, or may be an external device independent of the user interface terminal apparatus 300 and the wearable device 100.

Examples of the user interface terminal apparatus 300 include a smartphone, a tablet computer, and a personal computer. The user interface terminal apparatus 300 includes a display device and an input device. Typically, the display device and the input device correspond to a touch panel that integrally includes a display function and an input function. Alternatively, the input device may be independent of a display that is the display device. In this case, the input device may include, for example, a mechanical switch, a wheel, a mouse, a keyboard, a microphone used for sound input.

Figure 2:
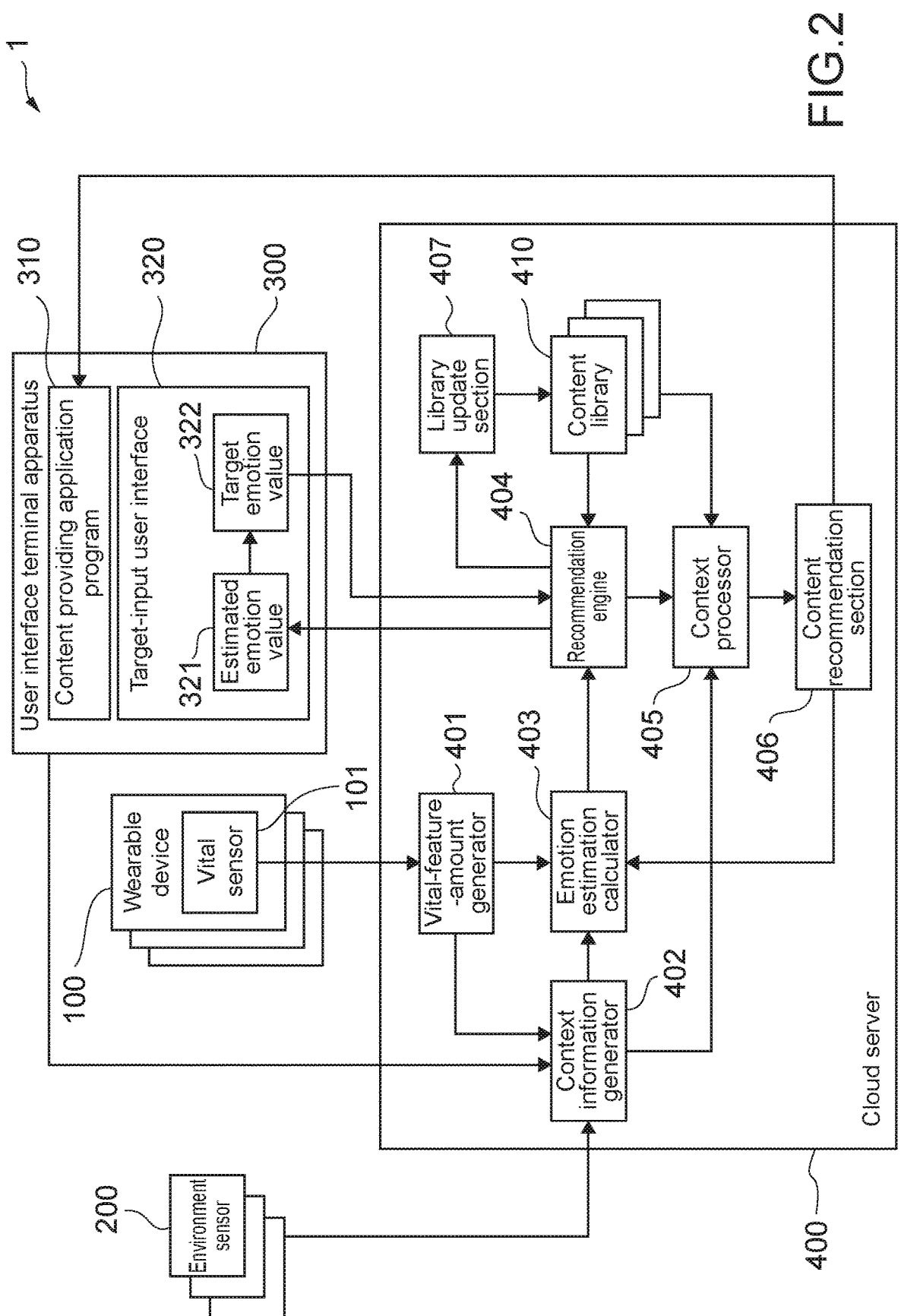
FIG. 2 illustrates a functional configuration of the content recommendation system.

The user interface terminal apparatus 300 executes a content providing application program 310 (refer to FIG. 2). The content providing application program 310 is a Web application that is provided by the user interface terminal apparatus 300 and the cloud server 400 working cooperatively. The content providing application program 310 recommends content (such as a piece of music and a moving image) to a user and provides the recommended content to the user (by, for example, streaming).

Further, the user interface terminal apparatus 300 acquires, from the wearable device 100, vital data of a user that is continuously and chronologically sensed by the vital sensor 101, and acquires environment data that is sensed by the environment sensor 200. The user interface terminal apparatus 300 determines an activity state of the user (such as whether the user is taking exercise) on the basis of, for example, the acquired vital data and environment data, position information (GPS information and wireless LAN information) that is acquired by the user interface terminal apparatus 300, and acceleration data. The content providing application program 310 may determine the activity state of the user. Alternatively, another application program (such as an application program that manages a fitness tracker) may determine the activity state of the user, and the content providing application program 310 may use information obtained by the determination.

The user interface terminal apparatus 300 regularly transmits, to the cloud server 400, vital data of a user that is continuously and chronologically sensed by the vital sensor 101, environment data that is sensed by the environment sensor 200, and information that indicates an activity state of the user that is determined by the user interface terminal apparatus 300. Note that the transmission of the data and information to the cloud server 400 that is performed by the user interface terminal apparatus 300 is merely an example. Instead, the wearable device 100 and the environment sensor 200 may respectively transmit the vital data and the environment data directly to the cloud server 400 without using the user interface terminal apparatus 300. Alternatively, the wearable device 100 may determine the activity state of the user on the basis of, for example, the vital data. In this case, the wearable device 100 may transmit the activity state of the user to the cloud server 400 through the user interface terminal apparatus 300 or without using the user interface terminal apparatus 300. In other words, any method may be adopted if the cloud server 400 is allowed to acquire the continuously and chronologically sensed vital data of the user, the environment data, and the information indicating the activity state of the user. Alternatively, the cloud server 400 may generate the information indicating the activity state of the user on the basis of information that indicates the received vital data and environment data.

The cloud server 400 is implemented by a plurality of hardware resources and a plurality of software resources. The cloud server 400 acquires continuously and chronologically sensed vital data of a user, environment data, and information that indicates an activity state of the user. On the basis of the vital data, the information indicating an environment state, and the activity state of the user, the cloud server 400 selects content to be recommended to the user, and recommends the selected content to the content providing application program 310 of the user interface terminal apparatus 300.

2. Functional Configuration of Content Recommendation System

FIG. 2 illustrates a functional configuration of the content recommendation system.

An information processing program stored in a ROM is loaded into a RAM and executed by a processor. Accordingly, the cloud server 400 operates as a vital-feature-amount generator 401, a context information generator 402, an emotion estimation calculator 403, a recommendation engine 404, a context processor 405, and a content recommendation section 406. The cloud server 400 stores a content library 410 in a non-transitory computer-readable storage apparatus. Note that at least a portion of the vital-feature-amount generator 401, the context information generator 402, and the emotion estimation calculator 403 that are a portion of the functional sections of the cloud server 400 may be implemented by the user interface terminal apparatus 300.

3. Flow of Operation of Content Recommendation System

Figure 3:
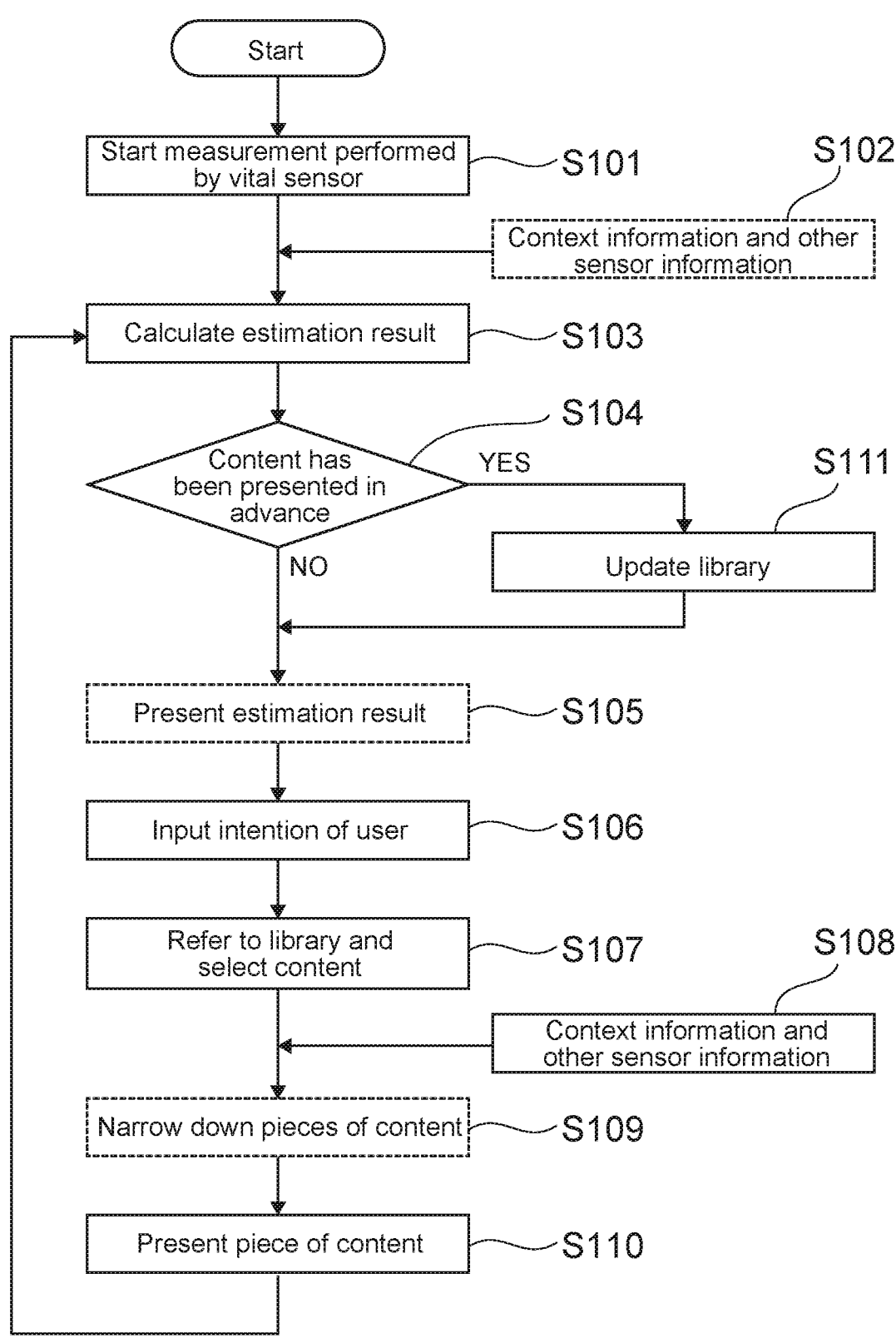
FIG. 3 illustrates a flow of an operation of the content recommendation system.

FIG. 3 illustrates a flow of an operation of the content recommendation system.

Step S101: Start Generating Vital-Feature-Amount Data

It is assumed that the vital sensor 101 of the wearable device 100 continuously and chronologically senses vital data (hereinafter referred to as chronological vital data) of a user without a trigger from the user interface terminal apparatus 300 or the cloud server 400.

When the vital-feature-amount generator 401 of the cloud server 400 acquires chronological vital data continuously and chronologically sensed by the vital sensor 101, the vital-feature-amount generator 401 starts generating chronological vital-feature-amount data from the chronological vital data, and continues to generate the vital-feature-amount data. In other words, the vital-feature-amount generator 401 starts acquiring chronological vital data, and then, without any other triggers, the vital-feature-amount generator 401 starts generating chronological vital-feature-amount data from the chronological vital data and continues to generate the vital-feature-amount data. For example, the vital-feature-amount generator 401 performs signal processing, such as denoising, on chronological vital data to generate chronological vital-feature-amount data.

Step S102: Generate Context Information

The context information generator 402 of the cloud server 400 generates context information regarding a user on the basis of chronological vital data (such as brain waves, pulse waves, a pulse, a blood pressure, a blood flow, sweating, breathing, and/or a temperature), environment data (such as a temperature, humidity, and illumination intensity), and/or an activity state of the user (such as whether the user is taking exercise). The context information may include any kinds of context such as a time, a location, and details of activities (for example, during taking exercise, during going to work, being at work, during driving, at the time of getting out of bed, and at the time of going to bed).

Step S103: Generate Estimated Emotion Value

The chronological vital-feature-amount data generated by the vital-feature-amount generator 401 and the context information generated by the context information generator 402 are input to the emotion estimation calculator 403 of the cloud server 400. The emotion estimation calculator 403 uses a model used to generate an estimated value of an emotion of a user (hereinafter referred to as an estimated emotion value) from the input chronological vital-feature-amount data and context information. The emotion estimation calculator 403 uses a model that uses the Russell's circumplex model. Note that only the chronological vital-feature-amount data may be input to the emotion estimation calculator 403 and the emotion estimation calculator 403 may generate an estimated emotion value on the basis of only the vital-feature-amount data (that is, without using the context information).

Not only newest vital-feature-amount data but also chronological vital-feature-amount data (that is, including previous vital-feature-amount data) is input to the emotion estimation calculator 403. The emotion estimation calculator 403 generates an estimated emotion value on the basis of newest vital-feature-amount data included in chronological vital-feature-amount data, the newest vital-feature-amount data being obtained by previous vital-feature-amount data included in the chronological vital-feature-amount data being changed. In other words, the emotion estimation calculator 403 generates a current estimated value of an emotion of a user, the value including information indicating how the previous vital-feature-amount data has been changed to the newest vital-feature-amount data. In other words, the emotion estimation calculator 403 generates a current estimated value of an emotion of a user, the value including information indicating how the previous vital-feature-amount data has been changed in a plurality of phases.

Figure 4:
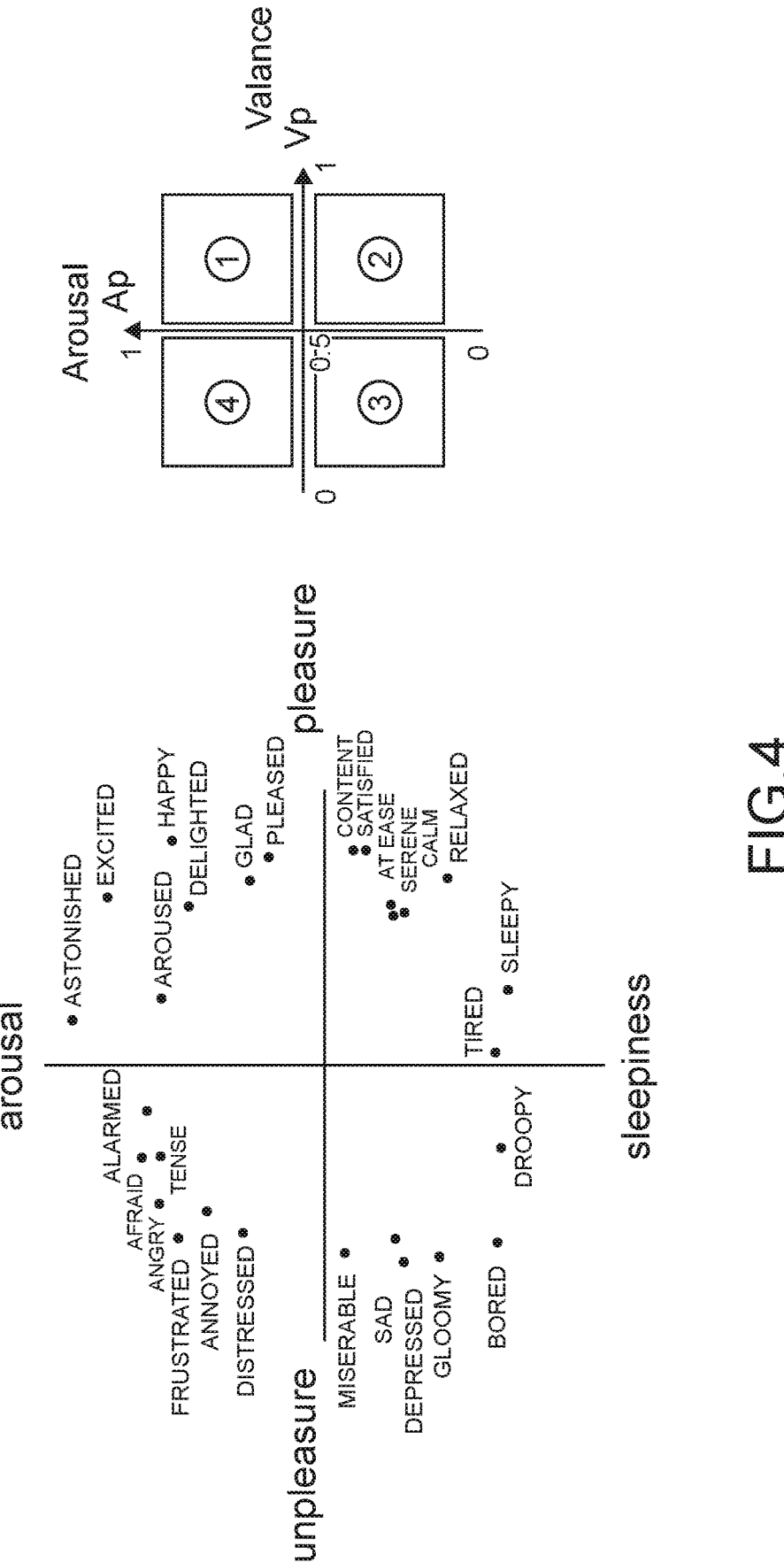
FIG. 4 is a diagram used to describe a model of an emotion estimation calculator.

FIG. 4 is a diagram used to describe a model of the emotion estimation calculator.

In the Russell's circumplex model, an arousal axis represents a degree of an emotion of a user in an arousal state in a range of from sleepiness to arousal, as illustrated on the left in the figure. Specifically, the arousal axis indicates a higher degree of arousal at a location situated closer to the top of the arousal axis and a lower degree of arousal (that is, a higher degree of sleepiness) at a location situated closer to the bottom of the arousal axis. Further, a valance axis represents a degree of the emotion of the user in a pleasure state in a range of from unpleasure to pleasure. Specifically, the valance axis indicates a more pleasant feeling at a location situated closer to a right end of the valance axis and a less pleasant feeling (that is, a more unpleasant feeling) at a location situated closer to a left end of the valance axis.

On the other hand, in the model of the emotion estimation calculator 403, an arousal axis represents the probability of a user having an emotion in an arousal state, and a valance axis represents the probability of the user having an emotion in a pleasure state, as illustrated on the right in the figure. The probability is represented by a statistical and probabilistic value, and is different from the "degree" adopted in the Russell's circumplex model. The probability corresponds to a value obtained by quantifying a state of a user having an emotion in a specific emotional state (an arousal state, a pleasure state). The use of the value obtained by the quantification makes it possible to estimate an emotion of a user more scientifically.

The emotion estimation calculator 403 calculates the probability of a user having an emotion in a specific emotional state using input chronological vital-feature-amount data, and sets the calculated probability to be an estimated emotion value. Specifically, the emotion estimation calculator 403 calculates the probability (a first probability) of a user having an emotion in an arousal state (a first specific emotional state). The emotion estimation calculator 403 calculates the probability (a second probability) of the user having an emotion in a pleasure state of valance (a second specific emotional state). The emotion estimation calculator 403 generates an estimated emotion value on the basis of the probability (the first probability) of a user having an emotion in an arousal state and the probability (the second probability) of the user having an emotion in a pleasure state. The calculation of probabilities in a plurality of types of emotional states results in increasing the possibility of being able to estimate an emotion of a user more precisely.

As illustrated on the right in the figure, the estimated emotion values are classified into four quadrants in a matrix, with a high or low probability of a user having an emotion in an arousal state and a high or low probability of the use having an emotion in a pleasure state being used in combination. When the calculated estimated emotion value is situated in an area (1), this means that the probability of a user having an emotion in an arousal state is high and the probability of the user having an emotion in a pleasure state is high. When the calculated estimated emotion value is situated in an area (2), this means that the probability of a user having an emotion in an arousal state is low and the probability of the user having an emotion in a pleasure state is high. When the calculated estimated emotion value is situated in an area (3), this means that the probability of a user having an emotion in an arousal state is low and the probability of the user having an emotion in a pleasure state is low. When the calculated estimated emotion value is situated in an area (4), this means that the probability of a user having an emotion in an arousal state is high and the probability of the user having an emotion in a pleasure state is low.

Note that the estimated emotion values do not necessarily have to be classified into four quadrants. The estimated emotion values may be classified into 16 quadrants obtained by each of the four quadrants being divided into "2×2". Further, each quadrant may be divided into smaller pieces (eventually, up to a coordinate level) to classify the estimated emotion values into a larger number of quadrants. Furthermore, only one of an arousal axis and a valance axis may be used to classify the estimated emotion values into two quadrants (for example, high and low probabilities in an arousal state). It is sufficient if the estimated emotion values are classified into at least two quadrants, as described above.

The emotion estimation calculator 403 inputs the generated estimated emotion value to the recommendation engine 404. It is assumed that, in this example, the estimated emotion value calculated by the emotion estimation calculator 403 is a value that indicates a low probability of a user having an emotion in an arousal state and a low probability of the user having an emotion in a pleasure state, and the estimated emotion value calculated by the emotion estimation calculator 403 is situated in the area (3).

In Step S104, the recommendation engine 404 of the cloud server 400 determines whether the recommendation engine 404 has recommended content to the user. When the recommendation engine 404 has determined that the recommendation engine 404 has never recommended content to the user before (Step S104, NO), the process moves on to Step S105.

Step S105: Display Estimated Emotion Value on Target-Input User Interface

The estimated emotion value generated by the emotion estimation calculator 403 is input to the recommendation engine 404 of the cloud server 400. The recommendation engine 404 supplies the user interface terminal apparatus 300 with the estimated emotion value generated by the emotion estimation calculator 403.

The user interface terminal apparatus 300 acquires an estimated emotion value from the cloud server 400. The user interface terminal apparatus 300 displays a target-input user interface 320 on a display device (such as a touch panel). The target-input user interface 320 is a GUI that is displayed to display an estimated emotion value 321 to a user and is displayed for the user to input an emotion (hereinafter referred to as a target emotion value) 322 that is a target of the user. In other words, the emotion that is a target of a user is a feeling that the user wants to have. Note that the content providing application program 310 may be used to display the target-input user interface 320. Alternatively, an application program that is independent of the content providing application program 310 may be used to display the target-input user interface 320.

Figures 5, 6:
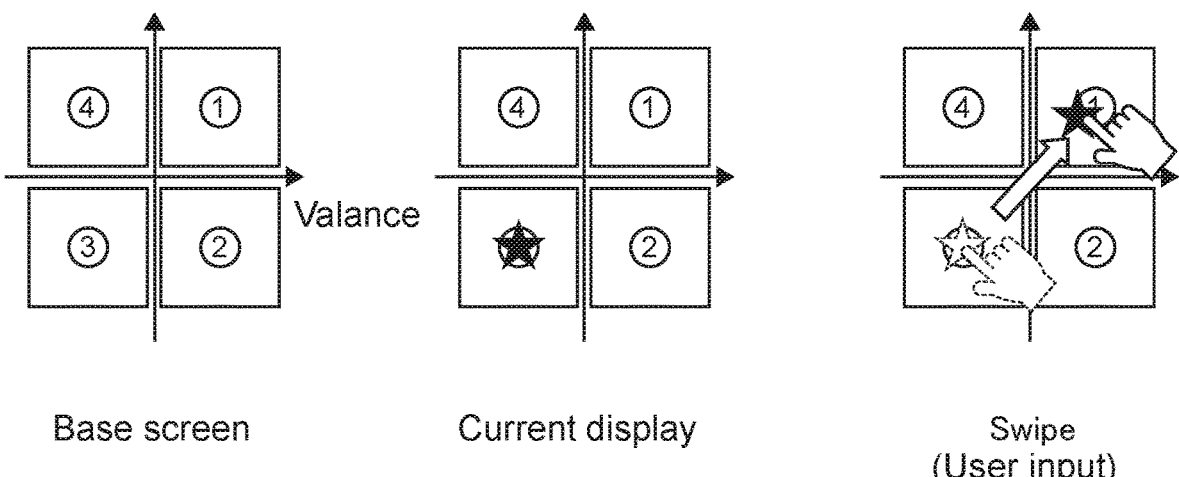
FIG. 5 illustrates an example of a target-input user interface.
FIG. 6 illustrates an example of a content library.

FIG. 5 illustrates an example of the target-input user interface.

As illustrated on the left in the figure, a base screen of the target-input user interface 320 is represented by a coordinate system in a matrix, as in the case of the model of the emotion estimation calculator 403. In other words, the base screen of target-input user interface 320 displays thereon a plurality of different areas (1) to (4) in a matrix in a biaxial direction, the plurality of different areas (1) to (4) being a plurality of different areas respectively corresponding to a combination of a high probability (first probability) of a user having an emotion in an arousal state (the first specific emotional state) and a high probability (second probability) of the user having an emotion in a pleasure state of valance (the second specific emotional state), a combination of the high first probability and a low second probability, a combination of a low first probability and the low second probability, and a combination of the low first probability and the high second probability.

As illustrated in a middle portion of the figure, the target-input user interface 320 displays an object (a star-shaped mark in this example) representing an estimated emotion value on the area (3) in which the estimated emotion value acquired from the cloud server 400 is situated.

When the user views the object displayed on the area (3), the user understands a relative location of the area (3) in the entirety of the coordinate system, where the object representing the estimated emotion value is displayed on the area (3). A user who is used to viewing the target-input user interface 320 visually understands that the probability of the user currently having an emotion in an arousal state is low and the probability of the user currently having an emotion in a pleasure state is low. Further, the user understands a relative evaluation of his/her current emotion. This enables the user to easily determine his/her target emotion. For example, when the user views the coordinate system of the target-input user interface 320, the user easily thinks of causing his/her emotion to reach another area of a target from the area (3). For example, the user thinks of causing a current estimated emotion value (the area (3): a low probability in an arousal state and a low probability in a pleasure state) to reach a target emotion value (the area (1): a high probability in an arousal state and a high probability in a pleasure state).

Step S106: Input Target Emotion Value

As illustrated on the right in the figure, the user selects one of the areas (the area (1) in the example). For example, the user swipes from the area (3) to the area (1), where the object representing the estimated emotion value is displayed on the area (3) and the target emotion value is situated in the area (1). The swiping enables the user to intuitively input the reaching of a current emotion to a feeling that the user wants to have. Further, the user may tap on the area (1) in which the target emotion value is situated. Furthermore, the user may say a number (1) of the area (1) in which the target emotion value is situated to perform input with sound. This results in the user inputting probabilities situated in the selected area (1) to the user interface terminal apparatus 300 as a target emotion value. As described above, a user selects one of the areas (the area (1) in this example), and this results in the user inputting, to the user interface terminal apparatus 300 and as a target emotion value, a combination of a first probability and a second probability (a high probability in an arousal state and a high probability in a pleasure state) that are situated in the selected area (1).

The user interface terminal apparatus 300 supplies the cloud server 400 with the target emotion value input by the user.

Step S107: Select Content from Content Library

The recommendation engine 404 of the cloud server 400 acquires the target emotion value input through the user interface terminal apparatus 300. The recommendation engine 404 selects, from the content library 410, content (such as a piece of music and a moving image) that is used to reach the target emotion value input by the user from the estimated emotion value generated by the emotion estimation calculator 403.

FIG. 6 illustrates an example of the content library.

The content library 410 stores therein at least one piece of content used to reach each one of a plurality of different target emotion values from a corresponding one of a plurality of different estimated emotion values. Specifically, the content library 410 is in the form of a two-dimensional matrix that includes a plurality of different estimated emotion values (1) to (4) and a plurality of different target emotion values (1') to (4'). A plurality of pieces of content (precisely, identification information regarding identification of content and access information regarding an access to content, and the same applies to the following description) used to reach each of the plurality of target emotion values from a corresponding one of the plurality of estimated emotion values, is registered in a portion corresponding to a point of intersection of lines corresponding to the estimated emotion value and the target emotion value. For example, a plurality of pieces of content is registered in a portion corresponding to a point of intersection of lines corresponding to the estimated emotion value (3) and the target emotion value (1'). Note that, typically, a plurality of pieces of content is registered in a portion corresponding to a point of intersection, but the number of pieces of content registered may be one. Different pieces of context information of a plurality of different pieces of context information are respectively associated with pieces of content of a plurality of pieces of content registered in a portion corresponding to a point of intersection. For example, as a piece of context information, "during taking exercise" is associated with a piece of content registered in a portion corresponding to a certain point of intersection, and, as a piece of context information, "at the time of going to bed" is associated with another pieces of content registered in the portion corresponding to the certain point of intersection.

Further, the content library 410 includes an initial content library 410 used as a reference, and a tailored content library 410 customized for each user. The recommendation engine 404 uses the initial content library 410 for a user to whom the recommendation engine 404 has never recommended content before (Step S104, NO). On the other hand, for a user to whom the recommendation engine 404 has recommended content, the recommendation engine 404 uses the content library 410 customized for each user (Step S104, YES).

The recommendation engine 404 selects a plurality of pieces of content from the content library 410. In this example, the recommendation engine 404 selects all of a plurality of pieces of content used to reach the target emotion value (1') from the estimated emotion value (3). In other words, the recommendation engine 404 selects all of a plurality of pieces of content registered in the portion corresponding to the point of intersection of the lines corresponding to the estimated emotion value (3) and the target emotion value (1').

Here, before the recommendation engine 404 acquires a target emotion value (Step S106), the vital-feature-amount generator 401 acquires chronological vital data to generate chronological vital-feature-amount data (Step S101), and the emotion estimation calculator 403 generates an estimated emotion value on the basis of the chronological vital-feature-amount data (Step S103). This makes it possible to reflect continuous and chronological vital data for a longer period of time, compared to when the recommendation engine 404 acquires a target emotion value, and then, chronological vital data is acquired to generate chronological vital-feature-amount data and an estimated emotion value is generated. This results in being able to generate an estimated emotion value more precisely. Since the estimated emotion value is more precise, content more suitable for reaching a target emotion value from the estimated emotion value can be selected.

Step S108: Input Context Information

Context information (Step S102) generated by the context information generator 402 is input to the context processor 405 of the cloud server 400.

Step S109: Narrow Down Pieces of Content

On the basis of the piece of context information generated by the context information generator 402, the context processor 405 of the cloud server 400 narrows down the plurality of pieces of content selected by the recommendation engine 404 to at least one piece of content. Typically, the context processor 405 narrows down pieces of content to one piece of content. However, the context processor 405 may narrow down pieces of content to a plurality of pieces of content. As described above, different pieces of context information of a plurality of different pieces of context information are respectively associated with pieces of content of a plurality of pieces of content registered in the content library 410. The context processor 405 narrows down a plurality of selected pieces of content to at least one piece of content with which a piece of context information generated by the context information generator 402 is associated. For example, the recommendation engine 404 selects a piece of content with which "during taking exercise" is associated as a piece of context information, and selects a piece of content with which "at the time of going to bed" is associated as a piece of context information. When the piece of context information generated by the context information generator 402 is "during taking exercise", the context processor 405 narrows down pieces of content to the piece of content with which "during taking exercise" is associated as a piece of context information. The context processor 405 may narrow down pieces of content not only on the basis of context information, but also on the basis of chronological vital data and metadata of content. For example, the context processor 405 may narrow down pieces of content to a piece of content (a piece of music) to which heartbeat of a user and its tempo that are included in chronological vital data synchronize.

Step S110: Recommend Content

The content recommendation section 406 of the cloud server 400 recommends, to the user interface terminal apparatus 300, the content obtained by the selection and the narrowing down.

The content providing application program 310 of the user interface terminal apparatus 300 supplies the recommended content (by, for example, streaming).

After Step S110: Loop

In the processes after the process of Step S101, the vital-feature-amount generator 401 of the cloud server 400 continues to generate chronological vital-feature-amount data. In other words, the vital-feature-amount generator 401 continues to update the chronological vital-feature-amount data by adding newest vital-feature-amount data.

From chronological vital-feature-amount data and context information that are obtained after the content recommendation section 406 recommends content, the emotion estimation calculator 403 generates an estimated emotion value after recommendation that is an estimated value of an emotion of a user (Step S103).

When the recommendation engine 404 of the cloud server 400 determines that the recommendation engine 404 has recommended content to the user (Step S104, YES), the process moves on to Step S111.

Step S111: Update Content Library

In this example, the cloud server 400 recommends, to a user, content used to reach the target emotion value (1') from the estimated emotion value (3) (Step S110). Thus, an emotion of the user is desired to reach the target emotion value (1') (that is, the probability of the user having an emotion in an arousal state is high and the probability of the user having an emotion in a pleasure state is high) after the user experiences (for example, viewing of) the content. In other words, the estimated emotion value after recommendation is desired to reach the target emotion value (1'). On the other hand, there is a possibility that the experience in (for example, viewing of) recommended content will not effectively act on a change in the emotion of the user and the estimated emotion value after recommendation will not reach the target emotion value (1'). For example, there is a possibility that the estimated emotion value after recommendation will remain unchanged at (3') or reach (2') or (4'). The calculation of an estimated emotion value after recommendation makes it possible to give feedback on whether recommended content has effectively acted on a change in an emotion of a user (that is, whether the target emotion value (1') has been reached).

A library update section 407 of the cloud server 400 updates a content library for each user by registering recommended content in the content library for each user as content used to reach, from an estimated emotion value, the estimated emotion value after recommendation. In this example, the library update section 407 labels the recommended content as content with high probabilities when the estimated emotion value after recommendation has reached the target emotion value (1') from the estimated emotion value (3).

On the other hand, when the estimated emotion value after recommendation remains unchanged at (3'), the library update section 407 deletes the recommended content from the portion corresponding to the point of intersection of the lines corresponding to the estimated emotion value (3) and the target emotion value (1') in the content library 410 of the user, and registers the recommended content in a portion corresponding to a point of intersection of the line corresponding to the estimated emotion value (3) and a line corresponding to the target emotion value (3'). When the estimated emotion value after recommendation reaches (2') or (4'), the library update section 407 deletes the recommended content from the portion corresponding to the point of intersection of the lines corresponding to the estimated emotion value (3) and the target emotion value (1') in the content library 410 of the user, and registers the recommended content in a portion corresponding to a point of intersection of the line corresponding to the estimated emotion value (3) and a line corresponding to the target emotion value (2') or (4').

As described above, the library update section 407 gives feedback on the content library 410 every time a piece of content is recommended. This makes it possible to change an initial content library 410 to a tailored content library 410 customized for each user.

Step S105: Display Estimated Emotion Value on Target-Input User Interface

An estimated emotion value after recommendation that is generated by the emotion estimation calculator 403 is input to the recommendation engine 404 of the cloud server 400.

The recommendation engine 404 supplies the user interface terminal apparatus 300 with the estimated emotion value after recommendation that is generated by the emotion estimation calculator 403.

The user interface terminal apparatus 300 acquires the estimated emotion value after recommendation from the cloud server 400. The user interface terminal apparatus 300 displays the target-input user interface 320 on a display device (such as a touch panel). The target-input user interface 320 displays an object (a star-shaped mark in this example) representing an estimated emotion value on an area in which the estimated emotion value after recommendation that is acquired from the cloud server 400 is situated.

When the user views the object displayed on the area, the user understands whether the estimated emotion value after recommendation has reached an area that is a target of the user (an area to which the user has swiped in Step S106).

Step S106: Input Target Emotion Value

When the estimated emotion value after recommendation has not reached the area that is a target of the user, the user may newly input a previously input estimated emotion value by swiping again to or tapping again on the area in which the previously input estimated emotion value is situated. Alternatively, when the user wants another area to be a target of the user, the user may newly input another target emotion value by swiping to or tapping on the other area. Note that, when an area that is a target of the user remains unchanged from an area on which input has been previously performed, it will not be a problem if the user does not perform input again on an area in which the target emotion value is situated.

When the user has newly input a target emotion value, the user interface terminal apparatus 300 supplies the cloud server 400 with the newly input target emotion value.

Step S107: Select Content from Content Library

The recommendation engine 404 of the cloud server 400 newly acquires the target emotion value input through the user interface terminal apparatus 300. The recommendation engine 404 selects, from the content library 410, content used to reach the target emotion value newly input by the user from the estimated emotion value after recommendation that is generated by the emotion estimation calculator 403.

On the other hand, when the user has not newly input the target emotion value, the recommendation engine 404 does not newly acquire the target emotion value from the user interface terminal apparatus 300. In this case, the recommendation engine 404 further selects, from the content library 410, content used to reach a previously input target emotion value from the estimated emotion value after recommendation. In this example, when the estimated emotion value after recommendation has reached the target emotion value (1') from the estimated emotion value (3), the recommendation engine 404 selects content used to reach the target emotion value (1') from the estimated emotion value (1) after recommendation. On the other hand, when the estimated emotion value after recommendation remains unchanged at (3'), the recommendation engine 404 selects content used to reach the target emotion value (1') from the estimated emotion value (3) after recommendation. When the estimated emotion value after recommendation has reached (2') or (4'), the recommendation engine 404 selects content used to reach the target emotion value (1') from the estimated emotion value (2) or (4) after recommendation.

Thereafter, the cloud server 400 inputs context information (Step S108), narrows down pieces of content (Step S109), and recommends a piece of content (Step S110), as in the case of the first round.

4. Method for Generating Content Library

Figures 7, 8:
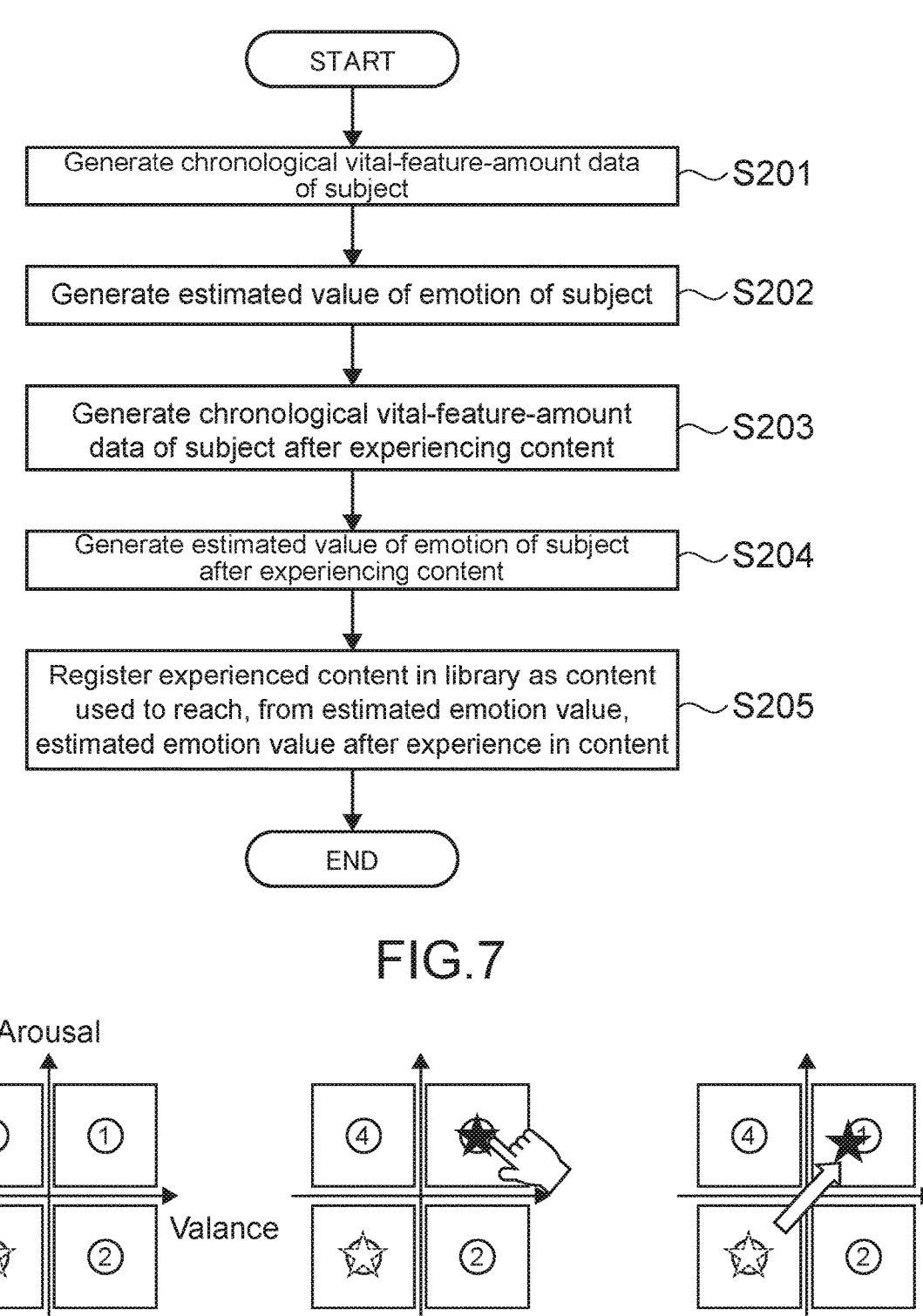
FIG. 7 illustrates a method for generating the content library.
FIG. 8 illustrates a target-input user interface according to a first modification.

FIG. 7 illustrates a method for generating the content library.

A method for generating an initial content library 410 used as a reference is described. An information processing apparatus (such as a computer, not illustrated) generates the initial content library 410 to store the generated initial content library 410 in the cloud server 400.

There is a plurality of (10 or more) subjects in a controlled environment without disturbance. Each of the plurality of subjects wears the wearable device 100 including the vital sensor 101. Each vital sensor 101 continuously and chronologically senses chronological vital data of a corresponding one of the plurality of subjects in the controlled environment.

A vital-feature-amount generator of the information processing apparatus acquires the chronological vital data of each of the plurality of subjects, the chronological vital data being sensed by a corresponding one of the vital sensors 101. The vital-feature-amount generator of the information processing apparatus generates pieces of chronological vital-feature-amount data of the plurality of subjects from the pieces of chronological vital data of the plurality of subjects. The vital-feature-amount generator of the information processing apparatus performs signal processing, such as denoising, on the pieces of chronological vital data of the plurality of subjects to generate pieces of chronological vital-feature-amount data of the plurality of subjects (Step S201).

An emotion estimation calculator of the information processing apparatus generates estimated emotion values of the plurality of subjects from the pieces of chronological vital-feature-amount data of the plurality of subjects. Further, the emotion estimation calculator of the information processing apparatus may generate the estimated emotion value using context information (Step S202).

Each of the plurality of subjects is caused to experience (for example, viewing of) content (such as a piece of music and a moving image) in the controlled environment. During the experience in content, each vital sensor 101 continuously and chronologically senses chronological vital data of a corresponding one of the plurality of subjects.

A vital-feature-amount generator of the information processing apparatus acquires pieces of chronological vital data of the plurality of subjects after experiencing the respective pieces of content, the pieces of chronological vital data being sensed by the respective vital sensors 101. On the basis of the pieces of chronological vital data of the plurality of subjects, the vital-feature-amount generator of the information processing apparatus generates pieces of chronological vital-feature-amount data of the plurality of subjects after experiencing the respective pieces of content (Step S203).

From the pieces of chronological vital-feature-amount data of the plurality of subjects after experiencing the respective pieces of content, the emotion estimation calculator of the information processing apparatus generates estimated emotion values respectively obtained after subjects of the plurality of subjects experience the respective pieces of content (Step S204).

A library update section of the information processing apparatus registers the experienced content in a small library as content used to reach, from an estimated emotion value, the estimated emotion value obtained after the subject experiences the content. The information processing apparatus generates and updates a plurality of small libraries by repeating this flow. According to a degree of similarity in content registered in a small library, or according to metadata of the content, the information processing apparatus associates context information with the content registered in the small library. The information processing apparatus integrates a plurality of small libraries to generate the content library 410 (Step S205). This makes it possible to scientifically generate an appropriate initial content library 410 without only depending on, for example, metadata or tempo of content.

II. SECOND EMBODIMENT

Hereinafter, descriptions and illustrations of a component, an operation, and the like that are similar to the component, the operation, and the like described above are omitted, and the description and the illustration are given focused on a component, an operation, and the like that are different from those described above.

In the first embodiment, the content library 410 is in the form of a two-dimensional matrix that includes a plurality of estimated emotion values (1) to (4) and a plurality of target emotion values (1') to (4'). The recommendation engine 404 selects, from the content library 410, content used to reach a target emotion value from a newest estimated emotion value that is included in estimated emotion values obtained in chronological order.

On the other hand, in a second embodiment, the recommendation engine 404 selects, from a content library, content used to reach a target emotion value from a newest estimated emotion value that is included in estimated emotion values obtained in chronological order, the newest estimated emotion value being reached from a previous estimated emotion value (for example, ten minutes ago) that is included in the estimated emotion values obtained in chronological order. In other words, the recommendation engine 404 selects content used to reach a target emotion value in a plurality of phases, where the target emotion value is reached from a newest estimated emotion value that is reached from a previous estimated emotion value. In other words, the recommendation engine 404 selects content that is used to reach a target emotion value that includes information indicating how a previous estimated emotion value has been changed to a newest estimated emotion value.

In order to achieve what has been described above, the content library stores therein at least one piece of content used to reach a target emotion value from a newest estimated emotion value that is included in estimated emotion values obtained in chronological order, the newest estimated emotion value being reached from a previous estimated emotion value that is included in the estimated emotion values obtained in chronological order. Specifically, the content library stores therein at least one piece of content used to reach, from each one of a plurality of different previous estimated emotion values, a corresponding one of a plurality of different newest estimated emotion values and to reach, from the corresponding one of the plurality of different newest estimated emotion values, a corresponding one of a plurality of different target emotion values.

Specifically, the content library is in the form of a three-dimensional matrix that includes a plurality of different previous estimated emotion values (1) to (4), a plurality of different newest estimated emotion values (1') to (4'), and a plurality of different target emotion values (1") to (4"). At least one piece of content used to reach, from each one of the plurality of previous estimated emotion values (1) to (4), a corresponding one of the plurality of newest estimated emotion values (1') to (4') and then to reach, from the newest estimated emotion value, a corresponding one of the plurality of target emotion values (1") to (4"), is registered in a portion corresponding to a point of intersection of lines corresponding to the estimated emotion value, the newest estimated emotion value, and the target emotion value.

III. MODIFICATIONS OF TARGET-INPUT USER INTERFACE

In the first embodiment, the base screen of target-input user interface 320 displays thereon a plurality of different areas (1) to (4) in a matrix in a biaxial direction, the plurality of different areas (1) to (4) being a plurality of different areas respectively corresponding to a combination of a high probability (first probability) of a user having an emotion in an arousal state (the first specific emotional state) and a high probability (second probability) of the user having an emotion in a pleasure state of valance (the second specific emotional state), a combination of the high first probability and a low second probability, a combination of a low first probability and the low second probability, and a combination of the low first probability and the high second probability, as illustrated in FIG. 5. The target-input user interface 320 displays an object (a star-shaped mark in this example) representing an estimated emotion value on the area (3) in which the estimated emotion value acquired from the cloud server 400 is situated.

A style of the target-input user interface is not limited to the example illustrated in FIG. 5. A plurality of modifications of the target-input user interface is illustrated and described below. Note that the style of the target-input user interface may be changeably settable by a user through the user interface terminal apparatus 300. Alternatively, the style of the target-input user interface may be uniquely determined by the specifications of an application.

1. First Modification

FIG. 8 illustrates a target-input user interface according to a first modification.

A base screen of the target-input user interface according to the first modification is similar to the base screen of FIG. 5. On the other hand, the target-input user interface according to the first modification does not display thereon an object representing an estimated emotion value (a dashed star-shaped mark is schematically illustrated). Thus, the user does not visually understand his/her current emotion. The user also selects one of the areas by, for example, tapping on the area or performing input with sound in this style. Accordingly, the user inputs probabilities situated in the selected area to the user interface terminal apparatus 300 as a target emotion value.

When the target-input user interface does not display thereon an object representing an estimated emotion value, the recommendation engine 404 of the cloud server 400 does not necessarily have to supply the user interface terminal apparatus 300 with an estimated emotion value generated by the emotion estimation calculator 403. Alternatively, the recommendation engine 404 of the cloud server 400 may supply the user interface terminal apparatus 300 with the estimated emotion value generated by the emotion estimation calculator 403. In this case, the user interface terminal apparatus 300 holds the estimated emotion value as internal information.

2. Second Modification

Figure 9:
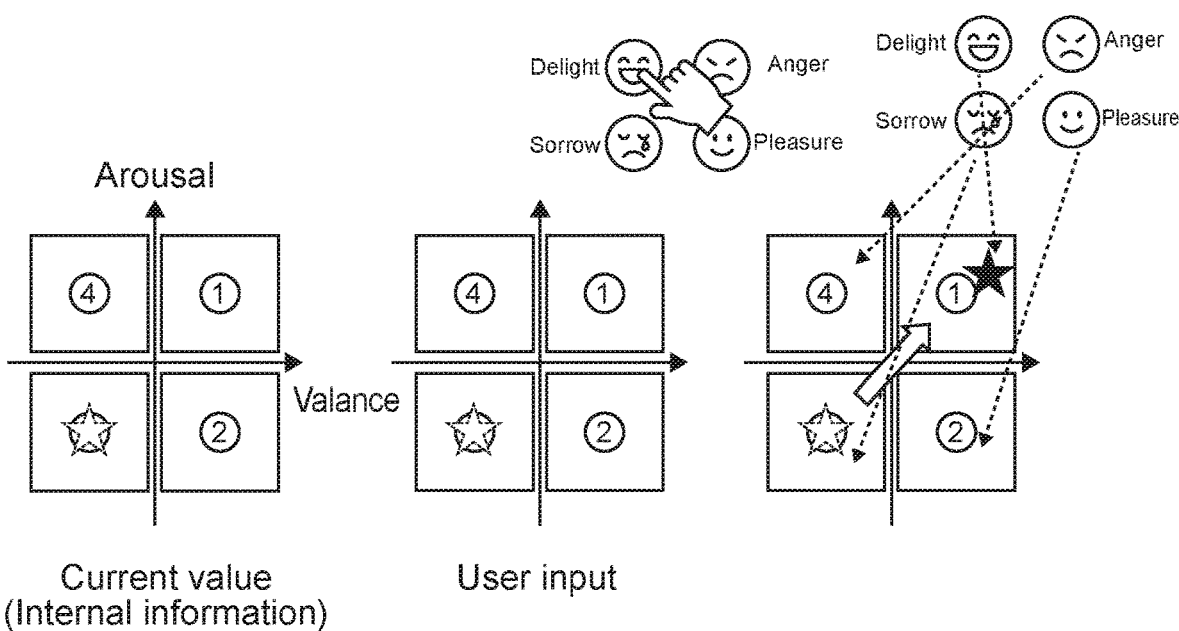
FIG. 9 illustrates a target-input user interface according to a second modification.

FIG. 9 illustrates a target-input user interface according to a second modification.

A base screen of the target-input user interface according to the second modification displays thereon a plurality of different areas in a matrix in a biaxial direction, the plurality of different areas being a plurality of different areas respectively corresponding to a combination of a high probability (first probability) of a user having an emotion in an arousal state (the first specific emotional state) and a high probability (second probability) of the user having an emotion in a pleasure state of valance (the second specific emotional state), a combination of the high first probability and a low second probability, a combination of a low first probability and the low second probability, and a combination of the low first probability and the high second probability. Not the numbers (1) to (4) but pictograms that represent respective emotional states respectively representing a combination of a high probability in one of the states and a high probability in another of the states, a combination of the high probability in the one of the states and a low probability in the other of the states, a combination of a low probability in the one of the states and the low probability in the other of the states, and a combination of the low probability in the one of the states and the high probability in the other of the states, are respectively displayed on (projected onto) the different areas of the plurality of different areas of the target-input user interface according to the second modification. For example, the pictogram may be a pictorial symbol in the form of a face, and may include a brief word of about one character.

Specifically, a pictogram that represents "delight" and is used to show that the probability in an arousal state is high and the probability in a pleasure state is high, is displayed on the area (1). A pictogram that represents "pleasure" and is used to show that the probability in an arousal state is low and the probability in a pleasure state is high, is displayed on the area (2). A pictogram that represents "sorrow" and is used to show that the probability in an arousal state is low and the probability in a pleasure state is low, is displayed on the area (3). A pictogram that represents "anger" and is used to show that the probability in an arousal state is high and the probability in a pleasure state is low, is displayed on the area (4).

The user can easily determine his/her target emotion by viewing a pictogram. Further, the user visually understands his/her current emotion easily when an object (a star-shaped mark in this example) representing an estimated value of an emotion of the user is displayed on a coordinate system on which a pictogram is displayed.

3. Third Modification

Figure 10:
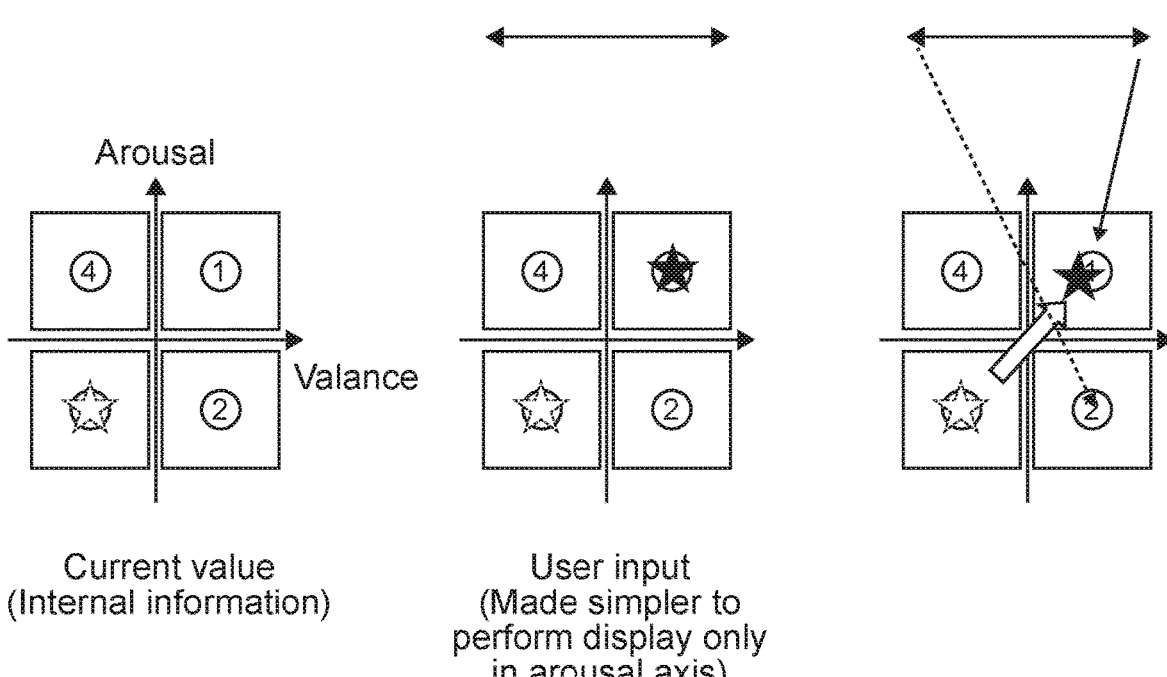
FIG. 10 illustrates a target-input user interface according to a third modification.

FIG. 10 illustrates a target-input user interface according to a third modification.

In the first embodiment, the base screen of target-input user interface 320 displays thereon a plurality of different areas (1) to (4) in a matrix in a biaxial direction, the plurality of different areas (1) to (4) being a plurality of different areas respectively corresponding to a combination of a high probability (first probability) of a user having an emotion in an arousal state (the first specific emotional state) and a high probability (second probability) of the user having an emotion in a pleasure state of valance (the second specific emotional state), a combination of the high first probability and a low second probability, a combination of a low first probability and the low second probability, and a combination of the low first probability and the high second probability.

On the other hand, the target-input user interface according to the third modification is made simpler to display thereon, in a single-axis direction, a plurality of different areas respectively corresponding to high and low probabilities in one of the specific emotional states. For example, it is assumed that a user does not select "unpleasure" but "pleasure" for valance in principle. Thus, the valance of a target emotion value is set to be fixed to "pleasure". In other words, the probability in the valence of a target emotion value is fixed at a positive value. The target-input user interface only receives input of a high or low probability in an arousal state as a target emotion value. In the case of the example illustrated in FIG. 5, the areas (3) and (4) in which the probability of being unpleasant in the valance axis is high is not displayed (or is displayed but input is not received), and the areas (1) and (2) in which the probability of being pleasant is high can be selected by a user. An area that is more likely to not be selected is not displayed, and only a necessary area is displayed. Accordingly, the entirety of the target-input user interface is made simpler. This enables a user to easily select a target area, and results in being less likely to be disadvantageous in that a desired area is not selectable.

4. Fourth Modification

Figure 11:
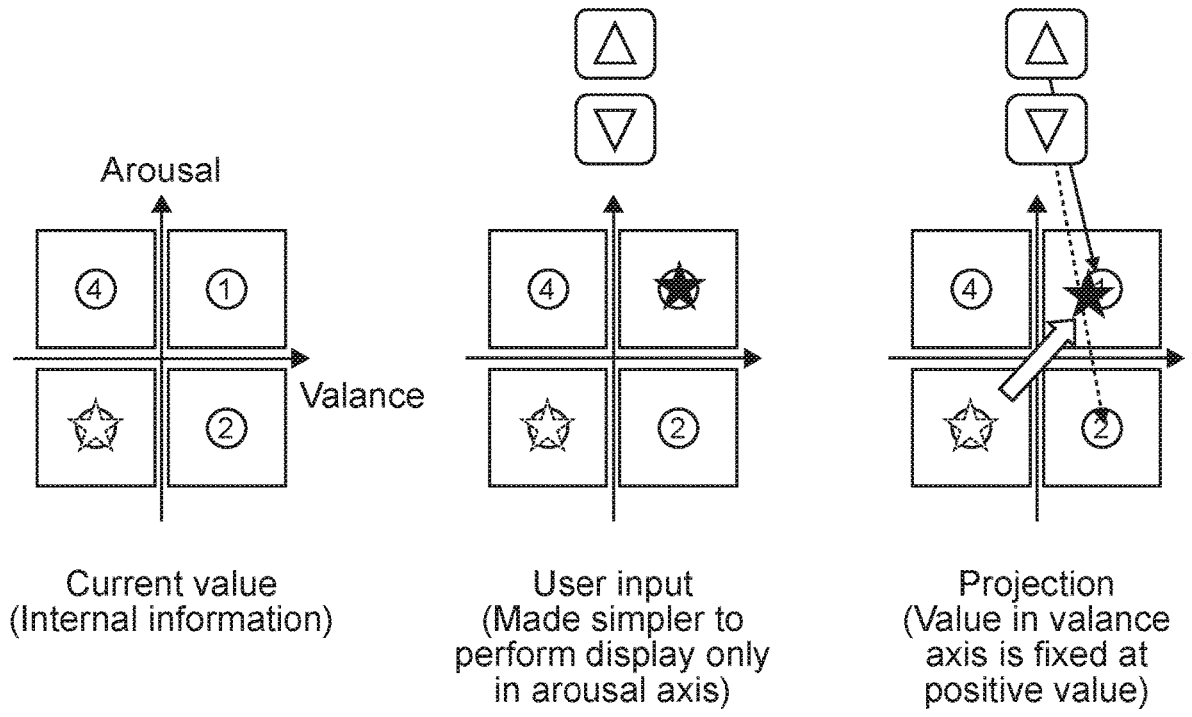
FIG. 11 illustrates a target-input user interface according to a fourth modification.

FIG. 11 illustrates a target-input user interface according to a fourth modification.

Instead of fixing the probability in valance and setting the probability in arousal to be changeable, as in the case of the third modification, the probability in arousal may be fixed and the probability in valance may be set to be changeable. In the third and fourth modifications, only a high or low probability in a single-axis direction is selected. This enables a user to perform input using a wheel or a mechanical switch as an input device.

IV. CONCLUSION

The present embodiment makes it possible to estimate an estimated value of an emotion of a user at all times, and to provide, on scientific grounds, content that is necessary and more specific to each individual, according to an estimated value of an emotion of a user and a target emotion value desired to be a target of the user. This results in being able to recommend content fit for each user, and to provide a recommendation system satisfactory to the user.

The present disclosure may also include the following configurations.

(1) A content recommendation system, including:
   a vital-feature-amount generator that
      acquires chronological vital data that is vital data of a user that is continuously and chronologically sensed by a vital sensor, and
      generates chronological vital-feature-amount data from the chronological vital data;
   an emotion estimation calculator that generates, from the chronological vital-feature-amount data, an estimated emotion value that is an estimated value of an emotion of the user;
   a recommendation engine that
      acquires a target emotion value that is input through a user interface terminal apparatus and indicates an emotion that is a target of the user, and selects, from a content library, content used to reach the target emotion value from the estimated emotion value; and
   a content recommendation section that recommends the selected content to the user interface terminal apparatus.
(2) The content recommendation system according to (1), in which
   before the recommendation engine acquires the target emotion value,
      the vital-feature-amount generator acquires the chronological vital data to generate the chronological vital-feature-amount data, and
      the emotion estimation calculator generates the estimated emotion value on the basis of the chronological vital-feature-amount data.
(3) The content recommendation system according to (1) or (2), in which
   the emotion estimation calculator generates the estimated emotion value on the basis of newest vital-feature-amount data included in the chronological vital-feature-amount data, the newest vital-feature-amount data being obtained by previous vital-feature-amount data included in the chronological vital-feature-amount data being changed.
(4) The content recommendation system according to any one of (1) to (3), in which
   the content library stores therein at least one piece of content used to reach each one of a plurality of the different target emotion values from a corresponding one of a plurality of the different estimated emotion values.
(5) The content recommendation system according to (4), in which
   the content library is in the form of a two-dimensional matrix that includes the plurality of the different estimated emotion values and the plurality of the different target emotion values, and
   at least one piece of content used to reach each one of the plurality of the different target emotion values from a corresponding one of the plurality of the different estimated emotion values, is registered in a portion corresponding to a point of intersection of lines corresponding to the one of the plurality of the different target emotion values and the corresponding one of the plurality of the different estimated emotion values.
(6) The content recommendation system according to any one of (1) to (5), in which
   the recommendation engine selects a plurality of pieces of content from the content library,
   the content recommendation system further includes:
      a context information generator that generates context information regarding the user; and
      a context processor that narrows down the plurality of selected pieces of content to at least one piece of content on the basis of the context information, and
   the content recommendation section recommends the at least one piece of content obtained by the narrowing down.
(7) The content recommendation system according to (6), in which
   the content library stores therein a plurality of pieces of content used to reach each one of a plurality of the different target emotion values from a corresponding one of a plurality of the different estimated emotion values, the different pieces of context information of a plurality of the different pieces of context information are respectively associated with pieces of content of the plurality of pieces of content, and the context processor narrows down the plurality of selected pieces of content to at least one piece of content with which the piece of generated context information is associated.

(8) The content recommendation system according to any one of (1) to (7), in which from the chronological vital-feature-amount data obtained after the content is recommended, the emotion estimation calculator generates an estimated emotion value after recommendation that is the estimated value of an emotion of the user, and the content recommendation system further includes a library update section that updates the content library for each user by registering the recommended content in the content library for each user as content used to reach, from the estimated emotion value, the estimated emotion value after recommendation.

(9) The content recommendation system according to any one of (1) to (8), in which from the chronological vital-feature-amount data obtained after the content is recommended, the emotion estimation calculator generates an estimated emotion value after recommendation that is the estimated value of an emotion of the user, the recommendation engine further selects, from the content library, content used to reach the target emotion value from the estimated emotion value after recommendation, and the content recommendation section recommends the further selected content to the user interface terminal apparatus.

(10) The content recommendation system according to any one of (1) to (9), in which the emotion estimation calculator generates the estimated emotion values obtained in chronological order, and the recommendation engine selects, from the content library, content used to reach the target emotion value from a newest estimated emotion value that is included in the estimated emotion values obtained in chronological order, the newest estimated emotion value being reached from a previous estimated emotion value that is included in the estimated emotion values obtained in chronological order.

(11) The content recommendation system according to (10), in which the content library stores therein at least one piece of content used to reach the target emotion value from the newest estimated emotion value included in the estimated emotion values obtained in chronological order, the newest estimated emotion value being reached from the previous estimated emotion value included in the estimated emotion values obtained in chronological order.

(12) The content recommendation system according to (10) or (11), in which the content library stores therein at least one piece of content used to reach, from each one of a plurality of the different previous estimated emotion values, a corresponding one of a plurality of the different newest estimated emotion values and to reach, from the corresponding one of the plurality of the different newest estimated emotion values, a corresponding one of a plurality of the different target emotion values.

(13) The content recommendation system according to (12), in which the content library is in the form of a three-dimensional matrix that includes the plurality of the different previous estimated emotion values, the plurality of the different newest estimated emotion values, and the plurality of the different target emotion values, and at least one piece of content used to reach, from each one of the plurality of the previous estimated emotion values, a corresponding one of the plurality of the newest estimated emotion values and to reach, from the corresponding one of the plurality of the newest estimated emotion values, a corresponding one of the plurality of the target emotion values, is registered in a portion corresponding to a point of intersection of lines corresponding to the one of the plurality of the previous estimated emotion values, the corresponding one of the plurality of the newest estimated emotion values, and the corresponding one of the plurality of the target emotion values.

(14) The content recommendation system according to any one of (1) to (13), in which the emotion estimation calculator calculates a probability of the user having an emotion in a specific emotional state, and sets the probability to be the estimated emotion value.

(15) The content recommendation system according to (14), in which the probability corresponds to a value obtained by quantifying a state of the user having an emotion in the specific emotional state.

(16) The content recommendation system according to (14) or (15), in which the emotion estimation calculator calculates a first probability that is a probability of the user having an emotion in a first specific emotional state, and a second probability that is a probability of the user having an emotion in a second specific emotional state, and generates the estimated emotion value on the basis of the first probability and the second probability.

(17) The content recommendation system according to (16), in which the first specific emotional state is an arousal state, the first probability is a probability of the user having an emotion in the arousal state, the second specific emotional state is a pleasure state of valance, and the second probability is a probability of the user having an emotion in the pleasure state.

(18) The content recommendation system according to any one of (14) to (17), in which the user interface terminal apparatus displays a target-input user interface that is a GUI displayed for the user to input the target emotion value, the target-input user interface displays thereon, in a single-axis direction, a plurality of different areas respectively corresponding to high and low probabilities in the specific emotional state, and the user selects one of the plurality of different areas to input the probability situated in the selected one of the plurality of different areas to the user interface terminal apparatus as the target emotion value.

(19) The content recommendation system according to (18), in which the target-input user interface displays thereon a plurality of different areas in a matrix in a biaxial direction, the plurality of different areas being a plurality of different areas respectively corresponding to a combination of a high first probability and a high second probability, a combination of the high first probability and a low second probability, a combination of a low first probability and the low second probability, and a combination of the low first probability and the high second probability, the first probability being a probability of the user having an emotion in a first specific emotional state, the second probability being a probability of the user having an emotion in a second specific emotional state, and the user selects one of the plurality of different areas to input, to the user interface terminal apparatus and as the target emotion value, a combination of the first and second probabilities situated in the selected one of the plurality of different areas.

(20) The content recommendation system according to (18) or (19), in which the user interface terminal apparatus acquires the generated estimated emotion value, and the target-input user interface displays an object representing the estimated emotion value on an area that is included in the plurality of different areas and in which the estimated emotion value is situated.

(21) The content recommendation system according to (20), in which the user inputs the target emotion value to the user interface terminal apparatus by swiping from the area displaying thereon the object representing the estimated emotion value to an area that is included in the plurality of different areas and in which the target emotion value is situated.

(22) The content recommendation system according to any one of (18) to (21), in which on respective areas of the plurality of different areas respectively corresponding to high and low probabilities in the specific emotional state, the target-input user interface displays pictograms that represent respective emotional states respectively representing the high and low probabilities.

(23) The content recommendation system according to any one of (1) to (22), in which the content library is generated by a process including acquiring pieces of chronological vital data of a plurality of subjects in a controlled environment, the pieces of chronological vital data being continuously and chronologically sensed by the respective vital sensors, generating pieces of chronological vital-feature-amount data of the plurality of subjects from the pieces of chronological vital data of the plurality of subjects, generating estimated emotion values of the plurality of subjects from the pieces of chronological vital-feature-amount data of the plurality of subjects, causing each of the plurality of subjects to experience a piece of content in the controlled environment, generating the pieces of chronological vital-feature-amount data of the plurality of subjects from the pieces of chronological vital data of the plurality of subjects after experiencing the respective pieces of content, from the pieces of chronological vital-feature-amount data of the plurality of subjects after experiencing the respective pieces of content, generating the estimated emotion values obtained after subjects of the plurality of subjects experience the respective pieces of content, and registering the piece of experienced content in the content library as a piece of content used to reach, from the estimated emotion value, the estimated emotion value obtained after the subject experiences the piece of content.

(24) The content recommendation system according to any one of (1) to (23), in which the vital sensor is included in a wearable device, and the vital sensor acquires, as the vital data, data of brain waves, pulse waves, a pulse, a blood pressure, a blood flow, sweating, breathing, and/or a temperature by brain wave measurement, plethysmography, skin conductance measurement, laser Doppler, image-capturing performed using an RGB camera, and/or image-capturing performed using a thermographic camera.

(25) The content recommendation system according to any one of (1) to (24), in which the context information generator generates the context information on the basis of the chronological vital-feature-amount data generated from the chronological vital data acquired by the vital sensor, environment data of an environment of the user, and/or an activity state of the user.

(26) The content recommendation system according to any one of (1) to (25), in which from the chronological vital-feature-amount data and the context information, the emotion estimation calculator generates the estimated emotion value that is the estimated value of an emotion of the user.

(27) A content recommendation method, including:

acquiring chronological vital data that is vital data of a user that is continuously and chronologically sensed by a vital sensor;

generating chronological vital-feature-amount data from the chronological vital data;

generating, from the chronological vital-feature-amount data, an estimated emotion value that is an estimated value of an emotion of the user;

acquiring a target emotion value that is input through a user interface terminal apparatus and indicates an emotion that is a target of the user;

selecting, from a content library, content used to reach the target emotion value from the estimated emotion value; and recommending the selected content to the user interface terminal apparatus.

(28) A content library that is generated by a process including:

acquiring pieces of chronological vital data of a plurality of subjects in a controlled environment, the pieces of chronological vital data being continuously and chronologically sensed by respective vital sensors;

generating pieces of chronological vital-feature-amount data of the plurality of subjects from the pieces of chronological vital data of the plurality of subjects;

generating estimated emotion values of the plurality of subjects from the pieces of chronological vital-feature-amount data of the plurality of subjects;

causing each of the plurality of subjects to experience a piece of content in the controlled environment;

generating the pieces of chronological vital-feature-amount data of the plurality of subjects from the pieces of chronological vital data of the plurality of subjects after experiencing the respective pieces of content;

from the pieces of chronological vital-feature-amount data of the plurality of subjects after experiencing the respective pieces of content, generating the estimated emotion values obtained after subjects of the plurality of subjects experience the respective pieces of content; and registering the piece of experienced content in the content library as a piece of content used to reach, from the estimated emotion value, the estimated emotion value obtained after the subject experiences the piece of content.

(29) A method for generating a content library, the method including:

acquiring pieces of chronological vital data of a plurality of subjects in a controlled environment, the pieces of chronological vital data being continuously and chronologically sensed by respective vital sensors;

generating pieces of chronological vital-feature-amount data of the plurality of subjects from the pieces of chronological vital data of the plurality of subjects;

generating estimated emotion values of the plurality of subjects from the pieces of chronological vital-feature-amount data of the plurality of subjects;

causing each of the plurality of subjects to experience a piece of content in the controlled environment;

generating the pieces of chronological vital-feature-amount data of the plurality of subjects from the pieces of chronological vital data of the plurality of subjects after experiencing the respective pieces of content;

from the pieces of chronological vital-feature-amount data of the plurality of subjects after experiencing the respective pieces of content, generating the estimated emotion values obtained after subjects of the plurality of subjects experience the respective pieces of content; and registering the piece of experienced content in the content library as a piece of content used to reach, from the estimated emotion value, the estimated emotion value obtained after the subject experiences the piece of content.

(30) A target-input user interface that is a GUI displayed by a user interface terminal apparatus for a user to input a target emotion value, the user interface terminal apparatus being included in a content recommendation system that includes a vital-feature-amount generator that acquires chronological vital data that is vital data of a user that is continuously and chronologically sensed by a vital sensor, and generates chronological vital-feature-amount data from the chronological vital data, an emotion estimation calculator that generates, from the chronological vital-feature-amount data, an estimated emotion value that is an estimated value of an emotion of the user, a recommendation engine that acquires the target emotion value being input through the user interface terminal apparatus and indicating an emotion that is a target of the user, and selects, from a content library, content used to reach the target emotion value from the estimated emotion value, and a content recommendation section that recommends the selected content to the user interface terminal apparatus, the target-input user interface displaying thereon, in a single-axis direction, a plurality of different areas respectively corresponding to high and low probabilities in a specific emotional state, the user selecting one of the plurality of different areas, the probability situated in the selected one of the plurality of different areas being input to the user interface terminal apparatus as the target emotion value.

The embodiments and the modifications of the present technology have been described above. Of course the present technology is not limited to the embodiments described above, and various modifications may be made thereto without departing from the scope of the present technology.

REFERENCE SIGNS LIST

1 content recommendation system
100 wearable device
101 vital sensor
200 environment sensor
300 user interface terminal apparatus
310 content providing application program
320 target-input user interface
321 estimated emotion value
322 target emotion value
400 cloud server
401 vital-feature-amount generator
402 context information generator
403 emotion estimation calculator
404 recommendation engine
405 context processor
406 content recommendation section
410 content library

The invention claimed is:

1. A content recommendation system, comprising:

a processor configured to:

acquire first chronological vital data that is vital data of a user, wherein the first chronological vital data of the user is continuously and chronologically sensed by a vital sensor;

generate first chronological vital-feature-amount data based on the first chronological vital data;

generate, based on the first chronological vital-feature-amount data, a first estimated emotion value, wherein the first estimated emotion value is a first estimated value of a first emotion of the user;

acquire a target emotion value based on a user input through a user interface terminal apparatus, wherein the target emotion value indicates an emotion that is a target of the user;

select, from a content library, a plurality of pieces of content, wherein the plurality of pieces of content is selected to reach the target emotion value from the first estimated emotion value;

generate context information regarding the user;

narrow down the selected plurality of pieces of content to at least one piece of content based on the context information; and recommend the at least one piece of content to the user interface terminal apparatus.

2. The content recommendation system according to claim 1, wherein the processor is further configured to acquire the first chronological vital data and generate the first estimated emotion value before the acquisition of the target emotion value.

3. The content recommendation system according to claim 1, wherein the processor is further configured to:

obtain newest vital-feature-amount data based on a change in previous vital-feature-amount data of the first chronological vital-feature-amount data; and generate a second estimated emotion value based on the newest vital-feature-amount data.

4. The content recommendation system according to claim 1, wherein the processor is further configured to store the at least one piece of content in the content library, the at least one piece of content is stored such that a corresponding estimated emotion value of a plurality of estimated emotion values reaches a respective target emotion value of a plurality of target emotion values, the corresponding estimated emotion value reaches the respective target emotion value based on a respective piece of content of the at least one piece of content, the plurality of target emotion values includes the target emotion value, and the plurality of estimated emotion values includes the first estimated emotion value.

5. The content recommendation system according to claim 4, wherein the content library is a two-dimensional matrix that includes the plurality of estimated emotion values and the plurality of target emotion values, the respective piece of content is registered in a portion of the content library, and the portion of the content library corresponds to a point of intersection of a first line corresponding to the target emotion value and a second line corresponding to the first estimated emotion value.

6. The content recommendation system according to claim 1, wherein the processor is further configured to:

store the plurality of pieces of content in the content library, wherein the plurality of pieces of content is stored such that a corresponding estimated emotion value of a plurality of estimated emotion values reaches a respective target emotion value of a plurality of target emotion values, the corresponding estimated emotion value reaches the respective target emotion value based on a respective piece of content of the plurality of pieces of content, and at least one piece of the context information of a plurality of pieces of the context information is associated with a respective piece of content of the plurality of pieces of content; and narrow down the selected plurality of pieces of content to the at least one piece of content based on the association of the at least one piece of the context information to the respective piece of content.

7. The content recommendation system according to claim 1, wherein the processor is further configured to:

obtain second chronological vital-feature-amount data based on the recommended at least one piece of content;

generate a second estimated emotion value based on the second chronological vital-feature-amount data, wherein the second estimated emotion value is a second estimated value of a second emotion of the user; and update the content library for the user based on registration of the recommended at least one piece of content in the content library, wherein the at least one piece of content is registered such that the first estimated emotion value reaches the second estimated emotion value, and the first estimated emotion value reaches the second estimated emotion value based on the at least one piece of content.

8. The content recommendation system according to claim 1, wherein the processor is further configured to:

obtain second chronological vital-feature-amount data based on the recommended at least one piece of content;

generate a second estimated emotion value based on the second chronological vital-feature-amount data, wherein the second estimated emotion value is a second estimated value of a second emotion of the user;

select, from the content library, content to reach the target emotion value from the second estimated emotion value, wherein the plurality of pieces of content one of includes or excludes the content; and recommend the selected content to the user interface terminal apparatus.

9. The content recommendation system according to claim 1, wherein the processor is further configured to:

generate a plurality of estimated emotion values in chronological order, wherein the plurality of estimated emotion values includes the first estimated emotion value; and select, from the content library, content to reach the target emotion value from a newest estimated emotion value among the plurality of estimated emotion values, wherein the newest estimated emotion value is reached from a previous estimated emotion value of the plurality of estimated emotion values, and the plurality of pieces of content includes the content.

10. The content recommendation system according to claim 9, wherein the processor is further configured to store the at least one piece of content in the content library, the at least one piece of content is stored such that the newest estimated emotion value reaches the target emotion value, and the newest estimated emotion value reaches the target emotion value based on the at least one piece of content.

11. The content recommendation system according to claim 9, wherein the processor is further configured to store the at least one piece of content of the plurality of pieces of content in the content library, the at least one piece of content is stored such that:

each of a plurality of previous estimated emotion values reaches a corresponding newest estimated emotion value of a plurality of newest estimated emotion values, wherein the each of the plurality of previous estimated emotion values reaches the corresponding newest estimated emotion value based on the at least one piece of content, and the plurality of estimated emotion values includes the plurality of previous estimated emotion values and the plurality of newest estimated emotion values; and the corresponding newest estimated emotion value reaches a respective target emotion value of a plurality of target emotion values, wherein the plurality of target emotion values includes the target emotion value.

12. The content recommendation system according to claim 11, wherein the content library is a three-dimensional matrix that includes the plurality of previous estimated emotion values, the plurality of newest estimated emotion values, and the plurality of target emotion values, the at least one piece of content is registered in a portion of the content library, and the portion of the content library is corresponding to a point of intersection of a first line corresponding to a previous estimated emotion value of the plurality of previous estimated emotion values a second line corresponding to the corresponding newest estimated emotion value, and a third line corresponding to the respective target emotion value.

13. The content recommendation system according to claim 1, wherein the processor is further configured to:

calculate a probability of the user having the first emotion in a specific emotional state; and set the probability as the first estimated emotion value.

14. The content recommendation system according to claim 13, wherein the probability corresponds to a value that quantifies a state of the user having the emotion in the specific emotional state.

15. The content recommendation system according to claim 13, wherein the probability includes a first probability and a second probability, and the processor is further configured to:

calculate the first probability of the user having a second emotion in a first specific emotional state;

calculate the second probability of the user having a third emotion in a second specific emotional state; and generate the first estimated emotion value based on the first probability and the second probability.

16. The content recommendation system according to claim 15, wherein the first specific emotional state is an arousal state, the first probability is a probability of the user having the second emotion in the arousal state, the second specific emotional state is a pleasure state of valance, and the second probability is a probability of the user having the third emotion in the pleasure state.

17. The content recommendation system according to claim 13, wherein the user interface terminal apparatus displays a first target-input user interface, the first target-input user interface is a Graphical User Interface (GUI) displayed for the user to input the target emotion value, the first target-input user interface includes, in a single-axis direction, a first plurality of different areas, each of the first plurality of different areas corresponds to a respective probability of each of a first probability in the specific emotional state and a second probability in the specific emotional state, one of the first plurality of different areas is selectable by the user to input the respective probability of a corresponding area of the first plurality of different areas, and the respective probability is input to the user interface terminal apparatus as the target emotion value.

18. The content recommendation system according to claim 17, wherein the user interface terminal apparatus displays a second target-input user interface, the second target-input user interface displays a second plurality of different areas in a matrix in a biaxial direction, a first area of the second plurality of different areas corresponds to a combination of a third probability and a fourth probability, a second area of the second plurality of different areas corresponds to a combination of the third probability and a fifth probability, a third area of the second plurality of different areas corresponds to a combination of a sixth probability and the fifth probability, a fourth area of the second plurality of different areas corresponds to a combination of the sixth probability and the fourth probability, the third probability and the sixth probability are probabilities of the user having a second emotion in a first specific emotional state, the fourth probability and the fifth probability are probabilities of the user having a third emotion in a second specific emotional state, and one of the second plurality of different areas is selectable by the user to input, to the user interface terminal apparatus, as the target emotion value.

19. The content recommendation system according to claim 17, wherein the user interface terminal apparatus acquires the generated first estimated emotion value, and the first target-input user interface displays an object that represents the first estimated emotion value on a first area of the first plurality of different areas.

20. The content recommendation system according to claim 19, wherein the target emotion value is input to the user interface terminal apparatus based on the user input, the user input corresponds to swipe from the first area to a second area of the first plurality of different areas, and the second area includes the target emotion value.

21. The content recommendation system according to claim 17, wherein the first target-input user interface displays a pictogram in each of the first plurality of different areas, and the pictogram represents the specific emotional state of a respective area of the first plurality of different areas.

22. The content recommendation system according to claim 1, wherein the content library is generated by an information processing apparatus that acquires a plurality of first pieces of chronological vital data of a plurality of subjects in a controlled environment, wherein the plurality of first pieces of chronological vital data includes the first chronological vital data, a set of pieces of chronological vital data of the plurality of first pieces of chronological vital data is continuously and chronologically sensed by a respective vital sensor of a plurality of vital sensors, each of the plurality of vital sensors is associated with a respective subject of the plurality of subjects, and the plurality of vital sensors includes the vital sensor;

generate a plurality of first pieces of chronological vital-feature-amount data of the plurality of subjects based on the plurality of first pieces of chronological vital data of the plurality of subjects, wherein the plurality of first pieces of chronological vital-feature-amount data includes the first chronological vital-feature-amount data;

generate a plurality of first estimated emotion values of the plurality of subjects based on the plurality of first pieces of chronological vital-feature-amount data of the plurality of subjects, wherein the plurality of first estimated emotion values includes the first estimated emotion value;

control each of the plurality of subjects to experience a piece of content of the plurality of pieces of content in the controlled environment;

generate a plurality of second pieces of chronological vital-feature-amount data of the plurality of subjects based on a plurality of second pieces of chronological vital data of the plurality of subjects, wherein the plurality of second pieces of chronological vital data of the plurality of subjects is acquired based on the experience of the piece of content by the respective subject;

a plurality of second estimated emotion values based on the plurality of second pieces of chronological vital-feature-amount data of the plurality of subjects; and register the piece of content in the content library based on the plurality of first estimated emotion values and the plurality of second estimated emotion values.

23. The content recommendation system according to claim 1, wherein the vital sensor is included in a wearable device, and the vital sensor acquires, as the vital data, at least one of data of brain waves, pulse waves, a pulse, a blood pressure, a blood flow, sweating, breathing, a temperature by brain wave measurement, plethysmography, skin conductance measurement, laser Doppler, image-capturing by an RGB camera, or image-capturing by a thermographic camera.

24. The content recommendation system according to claim 1, wherein the processor is further configured to generate the context information based on at least one of the first chronological vital-feature-amount data, environment data of an environment of the user, or an activity state of the user.

25. The content recommendation system according to claim 1, wherein the processor is further configured to generate the first estimated emotion value based on the first chronological vital-feature-amount data and the context information.

26. A content recommendation method, comprising:

acquiring chronological vital data that is vital data of a user, wherein the chronological vital data of the user is continuously and chronologically sensed by a vital sensor;

generating chronological vital-feature-amount data based on the chronological vital data;

generating, based on the chronological vital-feature-amount data, an estimated emotion value, wherein the estimated emotion value is an estimated value of an emotion of the user;

acquiring a target emotion value based on a user input through a user interface terminal apparatus, wherein the target emotion value indicates an emotion that is a target of the user;

selecting, from a content library, a plurality of pieces of content, wherein the plurality of pieces of content is selected to reach the target emotion value from the estimated emotion value;

generating context information regarding the user;

narrowing down the selected plurality of pieces of content to at least one piece of content based on the context information; and recommending the at least one piece of content to the user interface terminal apparatus.

27. A content library generation system, comprising:

a processor configured to:

acquire a plurality of first pieces of chronological vital data of a plurality of subjects in a controlled environment, wherein a set of pieces of chronological vital data of the plurality of first pieces of chronological vital data is continuously and chronologically sensed by a respective vital sensor of a plurality of vital sensors, and each of the plurality of vital sensors is associated with a respective subject of the plurality of subjects;

generate a plurality of first pieces of chronological vital-feature-amount data of the plurality of subjects based on the plurality of first pieces of chronological vital data of the plurality of subjects;

generate first estimated emotion values of the plurality of subjects based on the plurality of first pieces of chronological vital-feature-amount data of the plurality of subjects;

control each of the plurality of subjects to experience a piece of content in the controlled environment;

generate a plurality of second pieces of chronological vital-feature-amount data of the plurality of subjects based on a plurality of second pieces of chronological vital data of the plurality of subjects, wherein the plurality of second pieces of chronological vital data of the plurality of subjects is acquired based on the experience of the piece of content by the respective subject;

generate second estimated emotion values based on the plurality of second pieces of chronological vital-feature-amount data of the plurality of subjects;

register the piece of content in a content library based on the first estimated emotion values and the second estimated emotion values;

generate a current estimated emotion value of a subject of the plurality of subjects;

select, from the content library, a plurality of pieces of content, wherein the plurality of pieces of content is selected to reach a target emotion value of the subject from the current estimated emotion value of the subject, and the plurality of pieces of content includes the piece of the content;

generate context information regarding the subject;

narrow down the selected plurality of pieces of content to at least one piece of content based on the context information; and recommend the at least one piece of content to a user interface terminal apparatus associated with the subject.

28. A method for generating a content library, the method comprising:

by a processor of a content recommendation system:

acquiring a plurality of first pieces of chronological vital data of a plurality of subjects in a controlled environment, wherein a set of pieces of chronological vital data of the plurality of first pieces of chronological vital data is continuously and chronologically sensed by a respective vital sensor of a plurality of vital sensors, and each of the plurality of vital sensors is associated with a respective subject of the plurality of subjects;

generating a plurality of first pieces of chronological vital-feature-amount data of the plurality of subjects based on the plurality of first pieces of chronological vital data of the plurality of subjects;

generating first estimated emotion values of the plurality of subjects based on the plurality of first pieces of chronological vital-feature-amount data of the plurality of subjects;

controlling each of the plurality of subjects to experience a piece of content in the controlled environment;

generating a plurality of second pieces of chronological vital-feature-amount data of the plurality of subjects based on a plurality of second pieces of chronological vital data of the plurality of subjects, wherein the plurality of second pieces of chronological vital data of the plurality of subjects is acquired based on the experience of the piece of content by the respective subject;

generating second estimated emotion values based on the plurality of second pieces of chronological vital-feature-amount data of the plurality of subjects;

registering the piece of content in the content library based on the first estimated emotion values and the second estimated emotion values;

generating a current estimated emotion value of a subject of the plurality of subjects;

selecting, from the content library, a plurality of pieces of content, wherein the plurality of pieces of content is selected to reach a target emotion value of the subject from the current estimated emotion value of the subject, and the plurality of pieces of content includes the piece of the content;

generate context information regarding the subject;

narrowing down the selected plurality of pieces of content to at least one piece of content based on the context information; and recommending the at least one piece of content to a user interface terminal apparatus associated with the subject.

29. A content recommendation system, comprising:

a user interface terminal apparatus configured to display a target-input user interface, wherein the target-input user interface is a Graphical User Interface (GUI) to receive a target emotion value based on a user input, and the target emotion value indicates an emotion that is a target of a user; and a processor configured to:

acquire chronological vital data that is vital data of the user, wherein the chronological vital data of the user is continuously and chronologically sensed by a vital sensor;

generate chronological vital-feature-amount data based on the chronological vital data;

generate, based on the chronological vital-feature-amount data, an estimated emotion value, wherein the estimated emotion value is an estimated value of an emotion of the user;

acquire the target emotion value based on the user input through the user interface terminal apparatus; and select, from a content library, a plurality of pieces of content, wherein the plurality of pieces of content is selected to reach the target emotion value from the estimated emotion value;

generate context information regarding the user;

narrow down the selected plurality of pieces of content to at least one piece of content based on the context information; and recommend the at least one piece of content to the user interface terminal apparatus, wherein the target-input user interface includes, in a single-axis direction, a plurality of different areas, each of the plurality of different areas corresponds to a respective probability of a first probability in a specific emotional state and a second probability in the specific emotional state, and one of the plurality of different areas is selectable by the user to input the respective probability of a corresponding area of the plurality of different areas, wherein the respective probability is input to the user interface terminal apparatus as the target emotion value.

* * * * *